US008999323B2

(12) United States Patent
Liska et al.

(10) Patent No.: US 8,999,323 B2
(45) Date of Patent: Apr. 7, 2015

(54) COMPOSITION THAT CAN BE CURED BY POLYMERISATION FOR THE PRODUCTION OF BIODEGRADABLE, BIOCOMPATIBLE, CROSS-LINKABLE POLYMERS ON THE BASIS OF POLYVINYL ALCOHOL

(75) Inventors: Robert Liska, Schleinbach (AT); Jürgen Stampfl, Vienna (AT); Franz Varga, Mauerbach (AT); Heinrich Gruber, Vienna (AT); Stefan Baudis, Vienna (AT); Christian Heller, Vienna (AT); Monika Schuster, Vienna (AT); Helga Bergmeister, Vienna (AT); Günter Weigel, Vienna (AT); Claudia Dworak, Vienna (AT)

(73) Assignee: Technische Universität Wien, Schleinbach (AT)

(*) Notice: Subject to any disclaimer, the term of this patent is extended or adjusted under 35 U.S.C. 154(b) by 636 days.

(21) Appl. No.: 12/744,412

(22) PCT Filed: Nov. 21, 2008

(86) PCT No.: PCT/AT2008/000422
§ 371 (c)(1),
(2), (4) Date: Jul. 19, 2010

(87) PCT Pub. No.: WO2009/065162
PCT Pub. Date: May 28, 2009

(65) Prior Publication Data
US 2010/0303804 A1 Dec. 2, 2010

(30) Foreign Application Priority Data
Nov. 23, 2007 (AT) .................................. 1903/2007
Mar. 25, 2008 (AT) ..................................... 461/2008

(51) Int. Cl.
*A61K 39/395* (2006.01)
*A61K 38/16* (2006.01)
*C07C 271/10* (2006.01)
*C07C 271/20* (2006.01)
*C07C 271/22* (2006.01)
*C07C 69/96* (2006.01)
*C07F 9/113* (2006.01)
*C07F 9/40* (2006.01)
*C08F 2/46* (2006.01)
*A61L 27/56* (2006.01)

(52) U.S. Cl.
CPC ....................................... *A61L 27/56* (2013.01)

(58) Field of Classification Search
None
See application file for complete search history.

(56) References Cited

U.S. PATENT DOCUMENTS 6,001,128 A * 12/1999 Graff et al. ...................... 526/72
6,166,236 A * 12/2000 Bambury et al. ............. 556/420
8,129,441 B2 * 3/2012 Lafuente Cerda et al. ... 522/125
(Continued)

FOREIGN PATENT DOCUMENTS

EP 0 058 381 8/1985
WO 2005/073284 8/2005
(Continued)

OTHER PUBLICATIONS

International Search Report of International Publication No. WO 2009/065162, dated May 28, 2009.

*Primary Examiner* — Susan Tran
*Assistant Examiner* — William Craigo
(74) *Attorney, Agent, or Firm* — Drinker Biddle & Reath LLP

(57) ABSTRACT

The present invention relates to a polymerization-curable composition for the preparation of biodegradable, biocompatible, cross-linked polymers on the basis of polyvinyl alcohol comprising: 5 to 100% by weight of (a) vinyl ester monomer(s) of one of the general formulas (I) to (III):

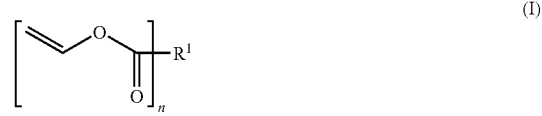

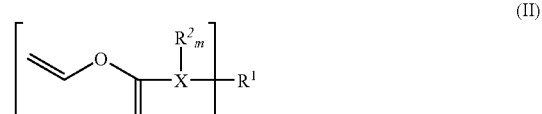

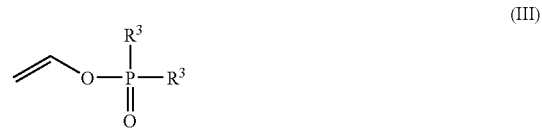

wherein X is oxygen, sulfur, nitrogen, or phosphorus; n is 1 to 1000, at least 20% of the n being $\geq 2$; the $R^1$ are selected from hydrogen; straight, branched or cyclic, saturated or unsaturated, n-valent hydrocarbon groups having 1 to 30 carbon atoms, which optionally have heteroatoms and are optionally substituted with one or more substituents selected from —OH, —COON, —CN, —CHO, and =O, and n-valent radicals of biodegradable, biocompatible oligomers and polymers; m is an integer from 1 to 5; the $R^2$ are selected from hydrogen, —OH, =O, and the options listed for $R^1$; and the $R^3$ are selected from hydrogen, —OH, and the options listed for $R^1$; 0 to 50% by weight of ethylenically unsaturated co-monomers; 0 to 10% by weight of (a) polymerization initiator(s); and 0 to 95% by weight of solvent(s).

16 Claims, 1 Drawing Sheet

(56) References Cited

U.S. PATENT DOCUMENTS

2003/0114552 A1* 6/2003 Schacht ................ 523/113
2007/0250169 A1* 10/2007 Lang .................. 623/17.12

FOREIGN PATENT DOCUMENTS

| WO | WO 2006077944 A1 | * | 7/2006 |
| WO | WO 2006108202 A1 | * | 10/2006 |

* cited by examiner

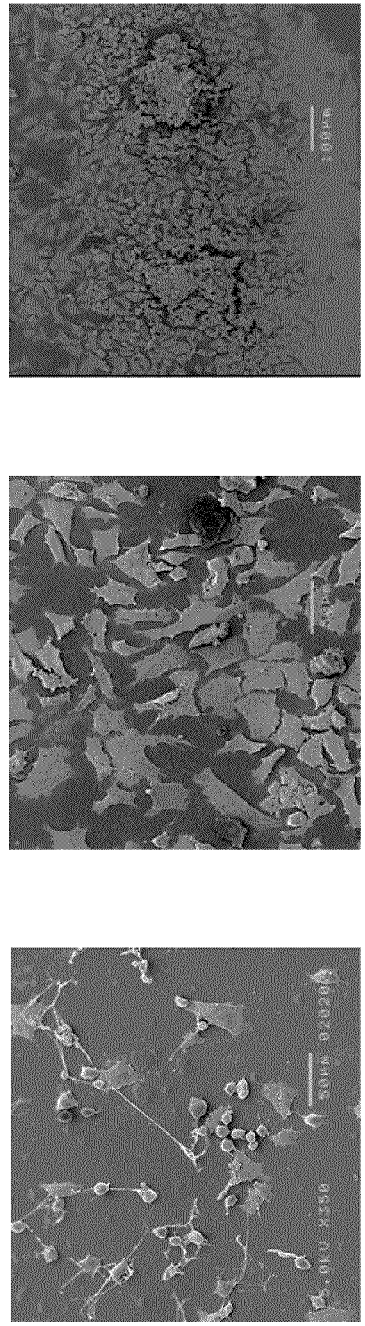

COMPOSITION THAT CAN BE CURED BY POLYMERISATION FOR THE PRODUCTION OF BIODEGRADABLE, BIOCOMPATIBLE, CROSS-LINKABLE POLYMERS ON THE BASIS OF POLYVINYL ALCOHOL

The present invention relates to polymerization-curable compositions for the preparation of biodegradable, biocompatible, cross-linked polymers on a polyvinyl alcohol basis.

STATE OF THE ART

For years, efforts have been made in the field of medical chemistry in order to develop biodegradable plastic materials and molded articles made thereof, which can be used as implants for the bodies of humans and animals and may, for example, serve as supporting or building materials for tissues (such as bones). To this end, the plastic materials and their degradation products need to be low in toxicity, on the one hand, and have to be easily workable and mechanically highly stable, on the other hand. Moreover, these materials should have a high affinity for cells such as osteoblasts, so that these can adhere to the surface of the molded article and initiate the formation of autologous bone material around the plastic. In this connection, it is especially desirable to use plastic material which dissolves in the course of time, the degradation products of which are resorbed by the body, and which, at the same time, is replaced by natural tissue such as bone tissue.

In the past, some success could be achieved by the use of polymers on the basis of polylactic acid and polyglycolic acid as well as on the basis of polylactones and polylactams, but these polymers are generally not cross-linked and, thus, mechanically relatively instable, and are dissolved too fast for some applications (bulk erosion). In order to overcome these disadvantages, co-polymers, e.g. block co-polymers, having cross-linkable groups such as fumaric acid were prepared (see, for example, T. Matsuda, M. Mizutani, S. Arnold, Macromolecules 33, 795-800 (2000), and M. Mizutani, T. Matsuda, Journal of Biomedical Materials Research 61(1), 53-60 (2002)). It turned out, however, that these materials have numerous disadvantages. On the one hand, the polymerizable basic compositions could often only be processed in the form of a melt or a solution, which are not only difficult to handle, but also cause high energy and material costs, since high amounts of heat are required and the solvent has to be removed. On the other hand, the cross-linking rates were low, and the form stability, the mechanical stability as well as the elasticity of the polymers were insufficient due to low cross-linking densities, so that their use as artificial bone material was practically impossible. The introduction of terminal acrylate groups caused an increase of the polymerization rate of the caproic acid derivatives (M. Mizutani, T. Matsuda, Journal of Biomedical Materials Research 62, 395 (2002)), but the other disadvantages could not be overcome.

The U.S. Patent Application No. 2004/0110439 describes biocompatible, cross-linked protein fibres for medical applications, which are spun from polymerized derivatives of biopolymers such as elastin, collagen, and gelatine and which optionally contain integrated living cells. However, due to their insufficient rigidity and elasticity, these materials are not suitable as, for example, bone substitutes, either.

A detailed overview of the problems can, for example, also be found in the applicant's WO 2006/108202, where compositions on an acrylate basis are described as a solution to said problems, which compositions optionally contain hydrolyzates of biopolymers such as gelatine, keratin, fibrin, or casein, and which are suitable for generative manufacturing procedures such as rapid prototyping or rapid manufacturing procedure. Thus, molded articles may be obtained in a relatively easy and economic way, the mechanical properties, including the porosity, of which articles are similar to those of bones, and which, optionally after surface modification, allow for good cell adherence.

In the course of continued research, the inventors found out, though, that the plastic materials described in WO 2006/108202 have the disadvantage that the degradation products of the molded articles on the basis of polyacrylate, i.e. acrylates, disclosed therein are unfavorably toxic for cells, also due to residual monomers, so that cells adhering thereto might die or that the adherence of further cells might be inhibited as soon as the biological degradation of the plastic material in the body starts.

In JP-A-09143194, Tokiwa Yutaka et al. describe the production of vinyloxycarbonyl-alkanoyl derivatives of sugars (i.e. of vinyl/sugar mixed esters of dialkanoic acids) by means of enzymatic glycosylation of divinyl esters of aliphatic dicarboxylic acids and the respective sugars in the presence of proteases of *Streptomycetes* or *Bacilli*. Maltose and divinyl adipate are the only examples for the sugars and the divinyl esters which are disclosed. The main focus lies on the preparation procedure. It is generally mentioned that the thus produced compounds might be suitable for use in polymer chemistry and in medicine, but there is no information pertaining to polymerizable compositions containing such compounds or to the properties of polymers produced therefrom or of three-dimensional articles made of these polymers.

In the Japanese Patent No. 2000-086806, the same inventor later describes details concerning the biodegradability of homopolymers of such compounds, explicitly of a homopolymer of vinyladipoylglucose, by microorganisms, which is said to amount to over 70% in one case. However, the degradation products produced in the course of the degradation are not mentioned.

In the Japanese Patent No. 2003-321624, the same inventor discloses coatings made of similar materials which are said to show good adherence to different surfaces, such as plastic materials, metals, paper, rubber, fibres, etc., biodegradability, and an affinity for proteins, nucleosides, nucleotides, nucleic acids, etc., thanks to which affinity said coatings may, for example, be used to detect them. Again, divinyl adipate is the only example mentioned for the divinyl ester starting material. The coatings are produced by immersing articles such as a film of polylactic acid in an aqueous solution of the vinyladipoylsugar in the presence of a ferrous sulfate/hydrogen peroxide catalyst system. Apart from the detection of different cell components, no other possible applications for such coatings are mentioned.

JP-A-2001-316465 describes the preparation of water-soluble linear polyesters from sugar alcohols and aliphatic dicarboxylic acids or their derivatives by means of enzymatic catalysis with lipase. Divinyl adipate and divinyl sebacate are mentioned as possible starting products from which linear polyesters of the respective sugar are produced with adipic or sebacic acid, apparently by an enzymatic transesterification comprising cleavage of vinyl alcohol.

A similar approach is disclosed in JP-A-11276188, where "polymeric sugar esters" are produced from divinyl sebacate in the presence of *Alcaligenes* bacteria producing lipase, i.e. apparently, again, polyesters are produced from sugar and dicarboxylic acid.

For some time it has been investigated whether biodegradable polymers are also suited for the reconstruction of soft connective and supporting tissues (blood vessels, heart valves, the abdominal wall, etc.). As with bones, the aim is a complete dissolution of the prosthetic material without a loss of function of the implant and with the new formation of organ-specific tissue. So far, natural (e.g. collagen and elastin) and artifical polymers (e.g. polyglycolic acid, polylactic acid, polydioxanone) have been used as starting materials for the preparation of implants. Graft degradation, which can hardly be controlled, and the occurrence of aneurysms connected thereto still constitute problems. Apart from that, a foreign body reaction, which should actually be prevented by the fast degradation/restructuring of the material in the body, is induced in the case of many implants. See L. Xue, H. P. Greisler, "Biomaterials in the development and future of vascular grafts", J. Vasc. Surg. 37, 472-480 (2003).

In the literature, vinyl carbonates and vinyl carbamates are also known for use in polymerization. WO 93/18070 A1 (corresponding to EP 629.214 B1) describes biodegradable polymers which are not cross-linked, which have a low water-solubility or are water-insoluble, and which contain lipophilic methylene diester groups of the following formula in their side chains:

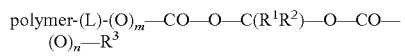

wherein m and n are 0 or 1, said groups in turn being cleavable by means of an esterase enzym, in order to yield a water-soluble residual polymer. L stands for an optional lipophilic linker. If m=1, the side chains contain carbonates. In one of the numerous embodiments, the polymer may be polyvinyl alcohol, so that, in the absence of the linker L, polymers comprising polyvinyl alcohol may be construed. However, not a single embodiment of WO 93/18070 A1 ist cross-linked, so that only linear polymers which can only have low to moderate mechanical strengths are described therein, which, for example, excludes their use as bone substitutes.

WO 2003/37944 describes various polysiloxanes being end capped with vinyl carbonate and having fluorinated side chains which are co-polymerized with 3-[tris(tri-methylsiloxy)silyl]propylvinyl carbonate and N-vinylpyrrolidone to yield hydrogels to be used as materials for contact lenses. The thus obtained hydrogels are cross-linked, but biodegradability of such co-polymers is not only not mentioned, but is even completely undesired in order to make them suitable for the use as materials for contact lenses.

WO 2006/71388 also describes polysiloxanes which are to be used as prepolymers for the preparation of biomedical devices (especially contact lenses) and which contain carbonate or carbamate groups in their chains. These prepolymers specifically have the following formula:

wherein M is a polymerizable, ethylenically unsaturated radical, Dii is a bivalent radical of a diisocyanate compound, PS is a bivalent radical of a polysiloxane diol or diamine, x is at least 2, and * represents a bivalent group of the formula —NH—CO—NH—, —NH—COO—, or —OCO—NH—. The groups M and PS may contain carbonate, ureido or urethane groups or also ether groups in their chains. In one of the numerous possible embodiments, M may have a terminal vinyl carbonate or vinyl carbamate group. The advantage mentioned for the presence of hydrophilic carbonate, carbamate or ureido groups is not cleavability, but an increase of the compatibility with hydrophilic co-monomers. 2-Methacryloyloxyethyl vinyl carbonate is mentioned as a possible co-monomer. Apart from their high tensile modulus, the advantage of plastic materials made from these prepolymers resides in their high oxygen permeability, which is required for the use as contact lenses. Biodegradability is again not desired. WO 2006/71479 and WO 2001/74932 of the same applicants also describe the preparation and coating of contact lenses, 2-methacryloyloxyethyl vinyl carbonate and N-(carboxyethyl)vinyl carbamate again being disclosed as possible co-monomers.

Thus, none of the polymers of the prior art would be suited for the use for highly stable materials such as bone substitute material or tooth filling material.

For this reason, the aim of the present invention was to provide an improved composition for the preparation of biocompatible plastic materials which may be used as body implants, especially as bone substitute material or as tooth filling material.

DISCLOSURE OF THE INVENTION

In a first aspect, the present invention reaches the above-described goal by providing a polymerization-curable composition for the preparation of biodegradable, biocompatible, cross-linked polymers, preferably on the basis of polyvinyl alcohol, said composition comprising:

a) 5 to 100% by weight of one or more vinyl ester monomers which are independently selected from compounds of one of the general formulas (I) to (III):

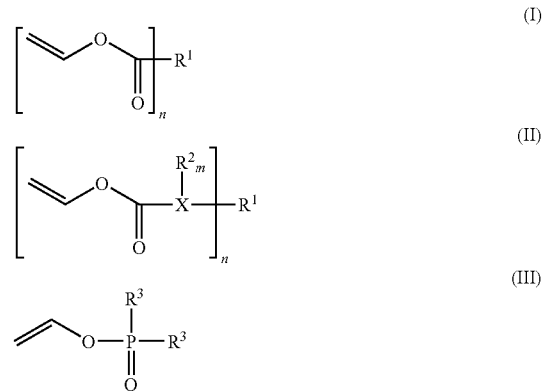

wherein

X is a heteroatom selected from oxygen, sulfur, nitrogen, and phosphorus; the n each independently are 1 to 1000, preferably 1 to 50, more preferably 1 to 20, even more preferably 1 to 20, even more preferably 1 to 20, even more preferably 1 to 10, and especially preferred 1 to 3, at least 20% of the n being ≥2;

the groups $R^1$ are independently selected from
  i) hydrogen; straight, branched or cyclic, saturated or unsaturated, n-valent hydrocarbon groups which have 1 to 30, preferably 3 to 25, more preferably 4 to 20, and especially preferred 5 to 15, carbon atoms, which optionally comprise one or more heteroatoms selected from oxygen, sulfur, nitrogen, and phosphorus within the chains and/or at the end of the chains, and which are optionally substituted with one or more substituents selected from —OH, —COON, —CN, —CHO, and =O, and
  ii) n-valent radicals of biodegradable, biocompatible oligomers and polymers selected from polysaccharides, polypeptides, polyamides, polyesters, polycarbonates, polyethers, and fatty acid derivatives;

m is an integer from 0 to 4;

the groups $R^2$ are selected from hydrogen, —OH, =O, and the options listed for $R^1$; and the groups $R^3$ are selected from hydrogen, —OH, and the options listed for $R^1$;

b) 0 to 50% by weight of one or more ethylenically unsaturated co-monomers selected from (meth)acrylic acid, maleic acid, fumaric acid, vinylpyrrolidon and α-olefin monomers;

c) 0 to 10% by weight of one or more polymerization initiators selected from thermal initiators and photoinitiators; and d) 0 to 95% by weight of one or more solvents selected from water, lower alcohols, ether, ketone, ester, amide and hydrocarbon solvents.

Apart from an optional solvent, the novel compositions of the invention thus comprise the following as main component(s):

one or more carboxylic acid vinyl ester(s) of the general formula (I) and/or one or more carbonic acid, thiocarbonic acid or carbamic acid vinyl ester(s) or one or more vinyloxycarbonyl-phosphorus compounds, preferably vinyloxycarbonyl derivatives of acids of phosphorus, especially of phosphonates, of the general formula (II) and/or one or more vinyl ester(s) of an acid of phosphorus, preferably one or more vinyl phosphates of the general formula (III)

being polymerizable monomers, which hereinafter will be all referred to as "vinyl esters".

As the composition is based on vinyl ester derivatives, polymerization thereof forms a polymer chain which partly, and preferably mainly, consists of polyvinyl alcohol. Thus, in the course of biodegradation of the polymer in the body, primarily polyvinyl alcohol and—at least intermediately—the corresponding free acids or partial esters, which, for simplicity's sake, hereinafter will be collectively referred to as "acids", and/or radicals of biodegradable oligomers and polymers will be formed. Polyvinyl alcohol is a non-toxic polymer which can often be found in drug formulations and is excreted without causing any harm to the body.

In the case of monomers of formula (I), fatty acids, sugar acids, or amino acids are formed, for example; according to the invention, especially those acids are used that can also be found in food and are thus harmless. This also holds true for the oligomers and polymers used as the component a)ii), which will hereinafter collectively be referred to as "biopolymers": as such, the invention uses biological substances or easily degradable plastic materials which are well tolerated and harmless for the organism. Further details can be found below.

In the case of monomers of formula (II), (thio)carbonic semiesters or carbamic acids are formed, for example, which all contain carboxyl groups attached to heteroatoms, are instable, and decarboxylate spontaneously. This means that there are no carboxyl groups left on the groups $R^1$ and that the only acid component formed is $CO_2$, which is expelled via the lungs. As there are no acid components left locally, compounds of formula (II) are preferred monomers in the compositions of the present invention.

In the case of monomers of formula (III), only acids of phosphorus, preferably phosphates, are formed in the body in the course of the degradation of the polymers, said acids being largely harmless and partly even required for substances produced naturally in the body.

Thus, a plastic material may be obtained from the above-described composition, which is stably cross-linked due to the presence of at least 20 mole percent of polyfunctional vinyl ester monomers (as 20% of the n are ≥2) and which may be introduced into the body without any problems due to its very low toxicity, if any. By adequately choosing parameters such as the ratio of mono- and polyfunctional vinyl ester monomers and the monomer content, hydrogels (for example, from compositions having a low monomer content, in water) or so called "PEG-o-gels" (i.e. with polyethyleneglycol as a solvent) as well as rigid, elastic articles (for example, from solvent-free compositions having a high content of polyfunctional monomers) may be formed and may then be used as tissue, cartilage or bone substitute materials or as tooth filling material, for example. Apart from that, the polymers thus obtained may be used as tissue supports, for example for heart valves, as a basic material for shunts and stents, and as glues or dressings (patches, for example) for tissue damage caused by injury or genetic disposition. Such formulations are also suited for the preparation of coatings for different substrates, for example for medical products and in other areas where a low toxicity of the monomers and polymers is desired, for example in contact with food.

The number of vinyl ester moieties in the composition is determined by the appropriate choice of the parameter n. If vinyl esters of biopolymers with high molecular weights, for example of over 10,000 or even over 1,000,000 g/mol, are used, for example, if starch is used as a biopolymer, up to 1,000 reactive sites, i.e. vinyl ester groups, may be present on the polymer backbone, depending on the degree of substitution. However, due to the high cross-linking density, which may be too high for some applications, as well as in order to increase the dissolution rates of the polymers in the body, fewer reactive sites, i.e. up to 50, up to 20, or up to 10 vinyl ester groups, per monomer molecule are also preferred as groups $R^1$ in the case of biopolymers. Especially if not biopolymers but monomers or short-chain oligomers (such as dimers) are used as $R^1$, preferably only up to 10, more preferably only up to 3, vinyl ester groups are present in the monomer molecule.

The value of the parameter m in formula (I), i.e. the number of substituents on the heteroatom X, except for the vinyl ester group and the $R^1$ group, may vary between 0 and the valence of the heteroatom X reduced by 2, which means that for oxygen m=0, for nitrogen m=1, for sulfur m=0 to 4, and for phosphorus m=0 to 3. If a polyfunctional group such as =O is bound to the heteroatom, the number of possible further substituents $R^2$ is, of course, reduced according to the valence of said group.

Moreover, two or more groups $R^1$ and $R^2$ can be connected to each other in order to form annular structures in which X is a ring atom. Formula (I) states that several vinyl ester/heteroatom moieties may be bound to a group $R^1$ and that one or more heteroatoms X may have more than one substituent $R^2$ selected from the options listed for $R^1$.

The number of carbon atoms of the group $R^1$ as the component A)i), which is not a biopolymer, amongst others depends on the respective value of n. Although compounds having very short chains such as divinyl(thio)carbonate or vinyl carbamate as well as long-chained radicals with up to 30 carbon atoms, being strongly branched or interrupted by cyclic structures, may be used, such very short-chained, very long-chained, or highly branched structures are not preferred according to the invention. Compounds having a very low molecular weight are difficult to handle due to their relative volatility, and long-chained or highly branched groups may be more difficult to decompose within the body. Thus, $R^1$ groups with 3 to 25 carbon atoms are rather preferred, among which groups those with 4 to 20 and especially with 5 to 15 carbon atoms are generally more preferred, even though the number of carbon atoms depends on the value of n, as has already been mentioned above. If $R^2$ is a group selected from the options listed for $R^1$, in view of mechanical and polymerization characteristics, the groups preferably are short-chained groups such as lower alkyl or alkoxy groups.

Vinyl ester monomers of formula (I) are thus preferably selected from aliphatic carboxylic acids and hydroxy carboxylic acids with 4 to 20 carbon atoms, sugar acids, amino acids as well as polymers and co-polymers of the above-mentioned acids, more preferably from the following acids and their derivatives: succinic acid, adipic acid, fumaric acid, citric acid, tartaric acid, aspartic acid, oxoglutaric acid, glutaminic acid, galactaric acid, ethylenediaminetetraacetic acid, butanetetracarboxylic acid, cyclopentanetetracarboxylic acid, polyglutamic acid, polyaspartic acid, hyaluronic acid, polylactic acid, polyglycolic acid, and poly(lactide-co-glycolide).

If $R^1$ is the residue of a biopolymer, said biopolymer may, for example, be selected from the following: polyethylene glycol, gelatine, chitosan, cellulose, amylose, and glycogen. This choice ensures that the degradation products of a polymer prepared from the composition of the invention are well tolerable or that the starting substances for the composition are readily available.

In the case of the vinyl ester monomers of formula (III), i.e. in the case of the vinyl esters of acids of phosphorus, the $R^3$ preferably are OH—, lower alkyl- or alkoxy groups or biopolymers or biooligomers. In some preferred embodiments, both $R^3$ groups are alkoxy groups, one of which especially preferably is another vinyloxy group, so that the monomer is a divinyl ester of the respective acid of phosphorus which serves as a cross-linker in the composition of the invention. In the case of other, especially preferred, variations, the vinyl ester monomers of formula (III) may be vinyl esters of nucleosides, nucleotides, or nucleic acids, in order to yield products in the course of the degradation, which may be used by the body.

The compositions of the present invention may only contain one vinyl ester monomer of one of the formulas (I) to (III), which monomer, however, then has to be at least bifunctional, i.e. a divinyl ester, in order to yield the required minimum cross-linking density upon polymerization. Thus, the compositions preferably contain several different vinyl ester monomers, e.g. one monofunctional and at least one bifunctional or higher functional monomer, since this makes the degree of cross-linking easier to control. If different vinyl ester monomers are present, they may all correspond to one of the formulas (I) to (III) or to different ones. This means that the compositions may contain, for example, combinations of vinyl carboxylates, vinyl carbonates or carbamates, and vinyl phosphates. The choice of such combinations is not specifically limited and may be selected freely depending on the respective application of the polymer which is to be prepared therefrom, as long as the desired properties of the cured product are obtained in the course of the polymerization.

In preferred embodiments, the at least one vinyl ester monomer accounts for at least 50, more preferably at least 70 and especially preferred at least 90 mole percent of all monomers contained, in order to yield a plastic in the course of polymerization, that contains a high content of polyvinyl alcohol, which establishes the above-described advantages of the present invention even better.

Moreover, at least 35, more preferably at least 50, mole percent of the vinyl ester monomers of the composition of the present invention preferably are bifunctional or higher functional monomers which function as cross-linkers and in which $n \geq 2$. No matter if the overall monomer content in the composition is low or high, this has the advantage of offering sufficient cross-linking density in order to guarantee form stability and desired mechanical properties such as hardness and stability.

The fact that further heteroatoms may optionally be present within the chain or at its end is due to the fact that biological molecules with the specified chain lengths such as in sugar (acid), amino acid or peptide or fatty acid radicals, from which the vinyl ester monomers of the present invention are prepared, often contain heteroatoms. The same holds true for the optional substituents, unsaturation and branching sites. The optional substituents may also serve the purpose of promoting the adherence of cells to the surface of a polymer prepared from the composition of the present invention, which will be described in more detail further below.

The vinyl ester monomers of the compositions of the present invention are either commercially available or may be prepared according to procedures known from literature or according to the procedures disclosed in the synthesis examples below. Those skilled in the art will understand that the reaction parameters may have to be changed correspondingly in order to synthesize further compounds not described herein. In order to prepare vinyl esters of formula (II) with sulfur as the heteroatom X, the protocol described in synthesis example 8 may, for example, be applied, using the corresponding thiol or a HS-group-containing amino acid such as cysteine, for example, whose other functionalities may be protected, if necessary, instead of ethylene glycol, and reacting it with chloroformic acid vinyl ester. Where appropriate, the reaction temperature may be increased (for example to room temperature), in order to compensate for the lower reactivity of thiols. Any other procedure yielding the desired compounds is also suited, in which connection the following literature references may be cited.

Carbonates:

R. A. Olofson and J. Cuomo, Tetrahedron Lett. 21(9), 819-22 (1980), describe the synthesis of isobutyl vinyl carbonate from trimethylsilyl vinyl ether and chlorofumaric acid isobutylester using benzyltrimethylammonium fluoride as a catalyst.

R. A. Olofson, Dang Vu Anh; D. S. Morrison, and P. F. De Cusati, J. Org. Chem. 55(1), 1-3 (1990), describe a one-step synthesis from chloro- or fluorofumaric acid esters and aldehyds using crown ether catalysis.

K. Rege, S. Hu, J. A. Moore, J. S. Dordick, and S. M. Cramer, J. Am. Chem. Soc. 126(39), 12306-12315 (2004), describe the chemoenzymatic and thus regioselective synthesis starting from methyleneoxime vinyl carbonate and alcohols.

Carbamates:

R. A. Olofson, B. A. Bauman, and D. J. Wancowicz, J. Org. Chem. 43(4), 752-4 (1978), describe the preparation of vinyl carbamates from the respective amine, phosgen, and di(ethanal-2-yl) mercury.

A. J. Duggan and F. E. Roberts, Tetrahedron Lett. 20(7), 595-8 (1979), describe a synthesis starting from the respective amine and S-phenyl vinyl thiocarbonate.

Thiocarbonates:

A. J. Duggan and F. E. Roberts, Tetrahedron Lett. 20(7), 595-8 (1979), describe the synthesis of S-phenyl vinyl thiocarbonate from thiochlorofumaric acid S-phenyl ester and vinyl alcohol.

R. A. Olofson and J. Cuomo, J. Org. Chem. 45(12), 2538-41 (1980), describe a similar synthesis from thiochlorofumaric acid S-phenyl ester and trimethylsilyl vinyl ether.

Other possible starting substances for the preparation of vinyl ester monomers comprise, for example, various mono- and polyalcohols, including sugar and sugar acid derivatives, e.g. various glycols, glycerine, cyclohexane dimethanol, hexanediol, hexanol, butanol, ethanol, dodecanol, trimethylol propane, stearyl tartrate, glucose, ribose, fructose, glycerine aldehyde, dihydroxyacetone, deoxyribose, cellobiose, glucopyranose, erythrose, threose, as well as their thio-analogues, amines and polyamines, amino acids (preferably essential amino acids), nucleotides and nucleobases, peptides, e.g. jeffamine, piperidine, ethylenediamine, hexamethylenediamine, diethylenetriamine, triethylenetetramine, 1,12-diamino-4,9-diazadodecane, 1,5,10-triazadecane, hexylamine, and dodecylamine, polymers and biopolymers, e.g. starch, cellulose, chitosan, alginate, hydroxyethyl cellulose, hydroxyethyl starch, hyaluronate, gelatine, casein, polyvinyl alcohol, poly(ethylene carbonate), poly(1,2-propylene carbonate), poly-caprolactonediol, but also two- and three-block-co-polymers such as PEG-caprolactone, PEG-glycols, PEG-lactides, PEG-ethylene carbonate, and PEG-propylene carbonate, as well as different compounds showing biological activities such as salicylic acid ethyl ester, ascorbinic acid, ubiquinone, gallic acid, citric acid, curcumin, retinol, calciferol, thiamine, diaminopyrimidine, just to mention a few.

If required, the optional co-monomers as components b) may be introduced to serve various purposes, for example, the purpose of surface modification to promote the adherence of cells, the purpose of firmly attaching certain components of the composition such as initiators or optional additives, for example, for fixing them at specific sites in the molecule, but also the purpose of modifying the mechanical properties of the polymerized product. Preferably, biocompatible, non-toxic compounds are used for this purpose, but small amounts of other compounds such as acrylic and methacrylic acid derivatives may also be used. This also depends on the other components of the composition as well as on the fact how and where these co-monomers are to be introduced into the polymer chain. Preferably the co-monomers used as the component b) are selected from (meth)acrylic anhydride, (meth)acrylic acid glycidyl ester, (meth)acryloyloxy succinic anhydride, (meth)acryloyloxymethyl succinic anhydride, (meth)acrylic acid 2-oxo-1,3-dioxolanylmethyl ester, vinyl succinic anhydride, vinylene carbonate, and maleic anhydride, as these derivatives are relatively well tolerated and/or easily bind to desired partners such as functionalities on cell surfaces, additives, or initiators. Co-monomers undergoing free-radical ring-opening polymerization, e.g. cyclic carbonates, are suitable as well, since they interrupt the polyvinyl alcohol backbone and are cleavable in the body thus providing shorter polyvinyl alcohol chains which can be cleared more easily and rapidly.

In preferred embodiments of the present invention, at least one of the monomers or comonomers has functionalities which are able to bind to cell surfaces or receptors thereon by means of primary or secondary valences, e.g. by means of van der Waals forces or hydrogen bonds. On the one hand, this ensures good adherence of cells to the cured polymer, and on the other hand, living cells may be introduced into the composition as "additives", as this is known in the art, and may be immobilized via these functionalities.

The composition may contain polymerization initiators, e.g. in the case of an UV/VIS-curable composition. However, polymerization may also be initiated thermally or by means of electron or gamma radiation without using an initiator, which is not preferred, though. In preferred embodiments of the invention, 0.1 to 10, preferably 0.2 to 5 and even more preferably 0.5 to 3, percent by weight of at least one polymerization initiator are contained as the component c), because curing the product may thus be carried out more cost-efficiently and more completely. It is even more preferred that the at least one initiator is a photoinitiator, especially an UV/VIS initiator, which makes the composition of the invention especially suited for rapid prototyping or rapid manufacturing procedures.

As already mentioned above, in view of some applications of the final product, for example, if the desired product is a hydrogel, the composition may contain a solvent. In many cases, a solvent-free composition is preferred, though, e.g. if the composition is used in rapid prototyping or rapid manufacturing procedures. If a solvent is used, this solvent preferably is water or another well tolerated solvent such as an alcohol, (poly)glycol, or (vegetable) oil.

By means of optional additives, the composition may be provided with desired properties. The amount of such additives is not specifically limited as long as the effects of the invention are not impaired. Preferably, the additives are selected from polymerization sensitisers and inhibitors, stabilizers, modifying agents, plasticizers, coloring agents, bioactive agents, cells such as osteoblasts and smooth muscle cells, thickeners, and filling agents. On the one hand, by means of these additives, plastic additives which are customary according to the state of the art may be introduced and, on the other hand, the behavior of the cured final product may be influenced. Thus, in especially preferred embodiments, the bioactive agents may be selected from drugs, proteins, and ligands of cell surface receptors. For example, thrombocyte aggregation inhibitors/blood-clotting inhibitors or immunosuppressants, but also peptides for influencing cell proliferation and cell differentiation may be introduced into the composition and/or may be attached to the surface of the cured polymer. Further, cell-selective proteins such as antibodies, e.g. anti-CD34 or anti-CD133, which may bind to stem or precursor cells via antigen/antibody-reactions, or complement inhibitors for preventing inflammations on the surface also belong to this group. Known agents for improving cell adherence such as carboxymethyl dextranes, proteoglycans, collagen, gelatine, glucosaminoglycans, fibronectin, lectins, polycations as well as natural and synthetic biological cell coupling agents such as RGD peptides may be introduced and/or attached to the surface. On the one hand, good cell adherence may be ensured this way and, on the other hand, the polymer obtained from the composition of the invention may function as drug carrier when used in combination with drugs—in addition to or instead of its function as a substitute or supporting material for specific body tissues.

Further possible filling materials include tricalcium phosphate, $Ca_3(PO_4)_2$, and hydroxyapatite, which, on the one hand, serve as a calcium source for the formation of bones and, on the other hand, improve the adherence of cells, as well as various organic fillers such as autologous serum or plasma of the transplant recipient.

One or more additives may also be bound covalently to monomers, e.g. to one or more of the above-mentioned co-monomers which may easily be derivatized, as explained above, in the form of esters or via other functionalities of the (co-)monomers. This will not only guarantee a more even distribution of the additive than could possibly be achieved in the case of mere physical mixing it with the other components of the composition, but also provide for the attachment of a specific component exclusively to the surface of the polymer, if the respective additive is added not before the other components have already been pre-cured. Especially preferably, at least one of these additives which are covalently bound to monomers or co-monomers is a bioactive agent such as a drug or an agent for promoting the cell adherence, since such an agent has to fulfil its function mainly at the surface of the final plastic material.

In a second aspect, the invention relates to a biodegradable, biocompatible, cross-linked polymer, preferably based on polyvinyl alcohol, which consists of an above described composition in its cured state. Preferably, such a polymer has functionalities on its surface which are able to bind to cell surfaces or receptors thereon via primary or secondary valences such as van der Waals forces or hydrogen bonds, in order to promote the adherence of cells. For example, one of the above-mentioned cell coupling agents may preferably be bound to the surface of the polymer of the invention. The type of this polymer is not specifically limited. For example, it may be a structural body, a coating on a substrate, or a film, but also a hydrogel or a "PEG-o-gel".

In a third aspect, the present invention relates to a method for preparing such a biodegradable, biocompatible, cross-linked polymer by polymerizing a composition of the present invention according to the first aspect. In some preferred embodiments of the procedure, one part of the composition may be pre-cured, whereafter the rest of the composition is added thereto, and the mixture is cured. This allows for a targeted attachment of some components of the composition to the surface. The thus obtained polymer may optionally be subjected to an post-treatment, for example for post-curing purposes, for removing or deactivating excess additives or residual (co-)monomers, for modifying the surface or mechanical properties, but also for sterilizing purposes in view of its use as a transplant. Post-treatments may include heat treatment, extraction, reprecipitation or surface treatments such as surface impregnations.

In methods of the invention, the polymerization may be initiated thermally or photochemically, as mentioned above. Photochemically initiated polymerization is preferably used for generative manufacturing procedures, e.g. in the case of rapid prototyping or rapid manufacturing procedures. Thus, complicated structures such as those of bones or bone pieces may be recreated rapidly, in a relatively cost-efficient way and accurately as to their dimensions. Due to their low toxicity, the compositions of the invention are also suited for being cured in vivo after having been applied directly to damaged tissue. They may, however, also be introduced into the body in an optionally degradable bag or the like, may then be adequately shaped, and may afterwards be cured in vivo or ex vivo.

In fourth and fifth aspects, the present invention relates to various new compounds suited for being used as polymerizable monomers or cross-linkers in the compositions of the invention or in a method of the invention, but also in various other applications, as well as to this very use in compositions or methods of the invention.

The invention will be described in further detailed with reference to the following illustrative and non-limiting examples.

EXAMPLES

Below, the chemical compounds used in the examples are listed in a table together with their abbreviations.

The superscript letters a) to e) refer to the commercial sources of supply of the respective starting and reference compounds, representing the following suppliers:
  a): TCI Europe
  b): Ivoclar Vivadent
  c): Cognis (Photomer4006 F)
  d): Sartomer (Sartomer 415)
  e): Sigma Aldrich

| Name | Structure |
| --- | --- |
| HVE[a] (hexanoic acid vinyl ester) | |
| DVE[a] (decanoic acid vinyl ester) | |
| PAVE (N-acetyl phenylalanine vinyl ester) | |
| AVE[a] (adipic acid divinyl ester) | |
| KVE (octanedioic acid divinyl ester) | |

-continued

| Name | Structure |
|---|---|
| SEVE (sebacic acid divinyl ester) | 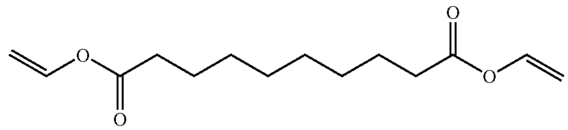 [SMILES: C=COC(=O)CCCCCCCCC(=O)OC=C] |
| DVMPL (diethylene glycol bis[O—(O'-vinylmaleinoyl)-polylactate]) | |
| TFVE (trimeric fatty acid trivinyl ester) | 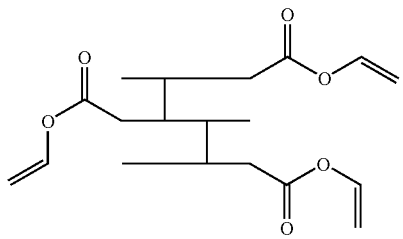 [SMILES: C=COC(=O)CC(C)C(C)C(CC(=O)OC=C)C(C)CC(=O)OC=C] |
| TUVE (ω,ω'-3,6,9-trioxaundecane-dioic acid divinyl ester) | 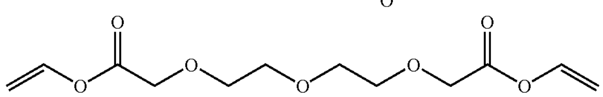 |
| EGDVC (ethylene glycol bis(vinyl carbonate)) | 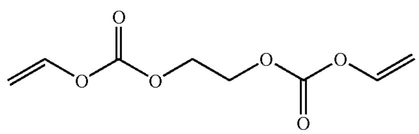 |
| BDDVC (1,4-butanediol bis(vinyl carbonate)) | 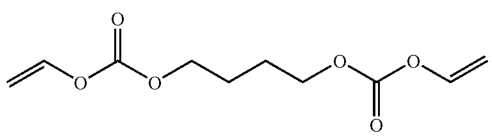 [SMILES: C=COC(=O)OCCCCOC(=O)OC=C] |
| HDDVC (1,6-hexanediol bis(vinyl carbonate)) | 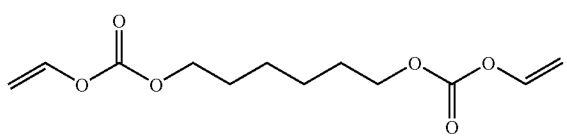 [SMILES: C=COC(=O)OCCCCCCOC(=O)OC=C] |
| GTVC (glycerine tris(vinyl carbonate)) | 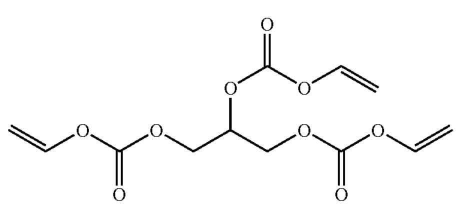 [SMILES: C=COC(=O)OCC(COC(=O)OC=C)OC(=O)OC=C] |
| DEGDVC (diethylene glycol bis(vinyl carbonate)) | 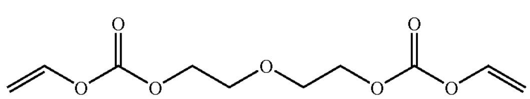 [SMILES: C=COC(=O)OCCOCCOC(=O)OC=C] |
| PEGDVC (polyethylene glycol(400) bis(vinyl carbonate)) | 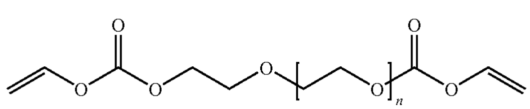 |
| CEVC (2-cyanoethyl vinyl carbonate) | 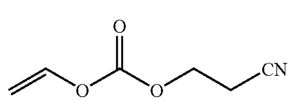 |

-continued

| Name | Structure |
|---|---|
| EVC (ethylvinyl carbonate) | 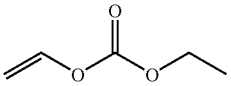 |
| RiTVC (ricinus oil tris(vinyl carbonate)) | 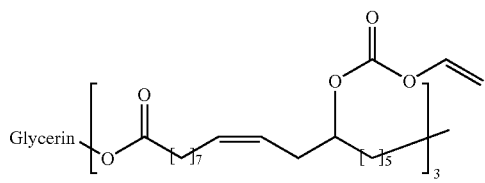 |
| HRiTVC (hydrated ricinus oil tris(vinyl carbonate)) | 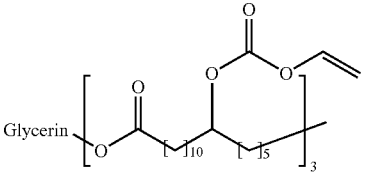 |
| DEG(PLAVC)$_2$ (diethylene glycol bis[O—(O'-vinyloxycarbonyl)-polylactate]) | 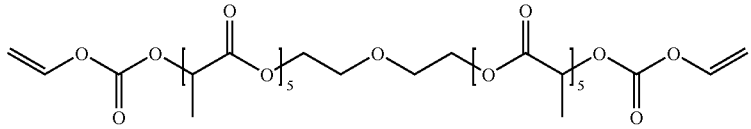 |
| DMEDDVCA (N,N'-dimethyl ethylenediamine bis(vinyl carbamate)) | 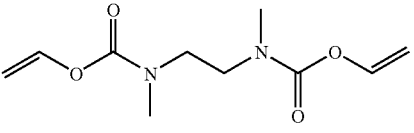 [SMILES: C=COC(=O)N(C)CCN(C)C(=O)OC=C] |
| PDVCA (piperazine bis(vinyl carbamate)) | 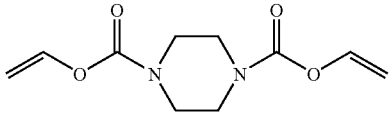 |
| JAVM (3,3'-ethylenedioxy bis(propylamine)divinyl carbamate) | 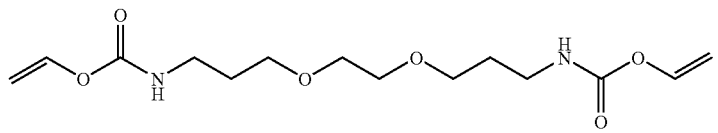 [SMILES: C=COC(=O)NCCCOCCOCCCNC(=O)OC=C] |
| EAVM (bis[ω-aminopolyethylene glycol(500)]amine tris(vinyl carbamate)) | 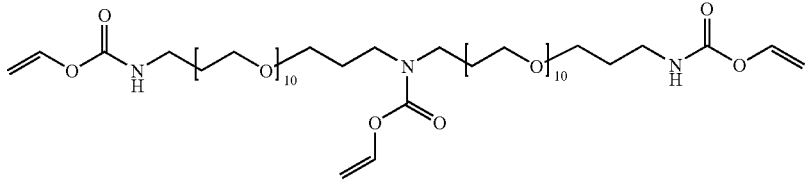 |
| SMEVCA (sarcosine methyl ester vinyl carbamate) | 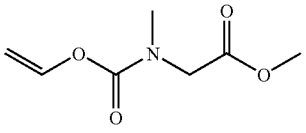 |
| MHADVC (N,O-bis(vinyloxy-carbonyl)-N-methylhydroxylamine) | 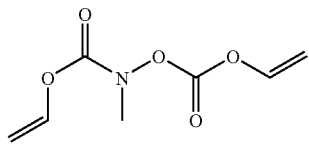 |

-continued

| Name | Structure |
|---|---|
| MVCA (N-methoxy vinyl carbamate) | 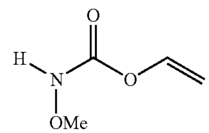 |
| AMVCA (N-acryloyl N-methoxy vinyl carbamate | 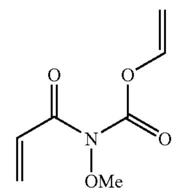 |
| VCPDE (vinyloxycarbonyl phosphonic acid diethyl ester) | 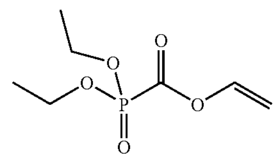 |
| EPEVC (2-diethoxyphosphoryloxy-ethylamine vinyl carbamate) | 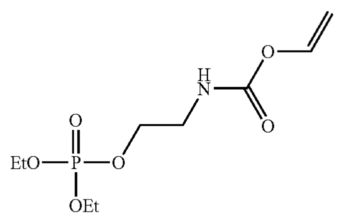 [SMILES: C=COC(=O)NCCOP(=O)(OCC)OCC] |
| EBVCAEP (ethyl bis[2-(vinyloxy-carbonylamino)ethyl]phosphate) | 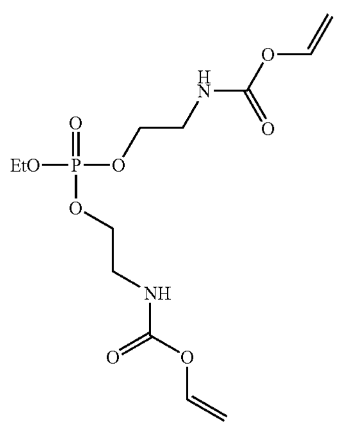 [SMILES: C=COC(=O)NCCOP(=O)(OCC)OCCNC(=O)OC=C] |
| DEVP (diethyl vinyl phosphate) | 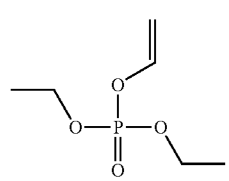 |
| DVEP (divinyl ethyl phosphate) | 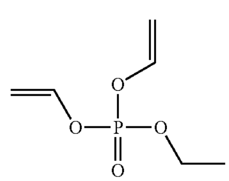 |

| Name | Structure |
|---|---|
| TVP (trivinyl phosphate) | 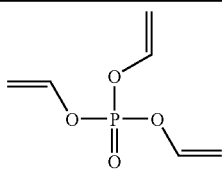 |
| References: Acrylates | |
| HDDA[c] (1,6-hexanediol diacrylate) | 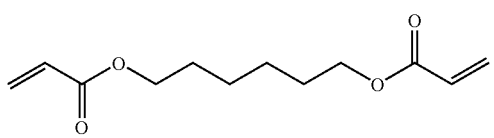 [SMILES: C=CC(=O)OCCCCCCOC(=O)C=C] |
| TTA[c] (trimethylolpropane triacrylate) | 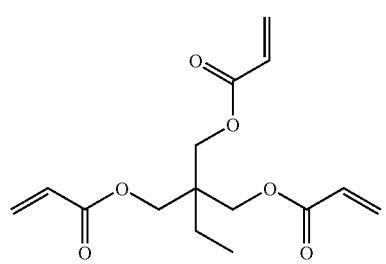 [SMILES: C=CC(=O)OCC(CC)(COC(=O)C=C)COC(=O)C=C] |
| ETA[d] (ethoxylated (20) TTA, MG 1200) | 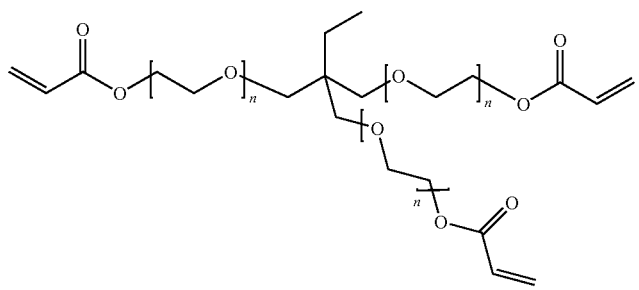 |
| PEGDA[e] (polyethylene glycol diacrylate, MG 800) | 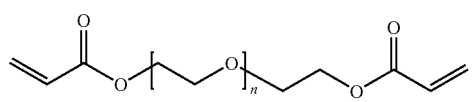 |
| Reference: Methacrylate | |
| BDMA[e] (1,4-butanediol dimethacrylate) | 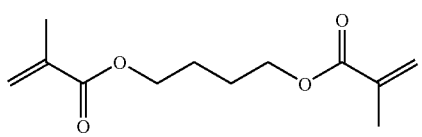 [SMILES: C=C(C)C(=O)OCCCCOC(=O)C(=C)C] |

Synthesis Example 1

Synthesis of sebacic acid divinyl ester (SEVE)

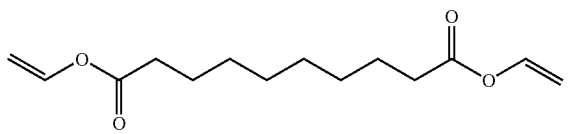 [SMILES: C=COC(=O)CCCCCCCCC(=O)OC=C]

15 g (74.2 mmol) of sebacic acid, 0.66 g (2.06 mmol) of mercury(II)acetate, and 0.12 g of hydroquinone were pre-charged in 75 ml of vinyl acetate into a 250 ml three-necked flask and stirred for 20 minutes under argon. Then, 0.09 g (0.01 mol) of p-toluenesulfonic acid were added as a catalyst, and the reaction mixture was refluxed for 4 hours. After cooling down to room temperature, the obtained solution was diluted with 200 ml ethyl acetate and extracted with 150 ml 2N NaOH. The organic phase was dried over $Na_2SO_4$, and the volatile components were removed on a rotary evaporator. Purification by flash column chromatography on silica gel (PE:EE=10:1) yielded 8.9 g (47% of th.) of a colorless liquid.

$^1$H-NMR ($CDCl_3$), δ (ppm): 7.25 (2H, dd, J=14.07/6.25 Hz, $H_2C$=C$\underline{H}$—); 4.84 (2H, dd, J=14.07/1.56 Hz, —HC=C (H)$\underline{H}$); 4.52 (2H, dd, J=6.25/1.56 Hz, —HC=C($\underline{H}$)H); 2.35 (4H, t, —CO—$CH_2$—); 1.62 (4H, $q_5$, —CO—$CH_2$—C$\underline{H}_2$—); 1.29 (8H, s, —$CH_2$—).

Synthesis Example 2

Synthesis of octanedioic acid divinyl ester (KVE)

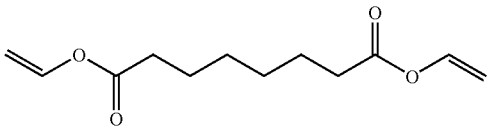 [SMILES: C=COC(=O)CCCCCCC(=O)OC=C]

The synthesis was carried out analogously to synthesis example 1. Purification by flash column chromatography on silica gel (PE:EE=10:1) yielded 11.4 g (47% of th.) of a colorless liquid.

$^1$H-NMR (CDCl$_3$), δ (ppm): 7.26 (2H, dd, J=13.84/6.21 Hz, H$_2$C=CH—); 4.85 (2H, dd, J=13.84/1.47 Hz, —HC=C(H)H); 4.54 (2H, dd, J=6.21/1.47 Hz, —HC=C(H)H); 2.37 (4H, t, —CO—CH$_2$—); 1.65 (4H, q$_5$, —CO—CH$_2$—CH$_2$—);1.48-1.25 (4H, m, —CH$_2$—).

Synthesis Example 3

Synthesis of N-acetyl phenylalanine vinyl ester (PAVE)

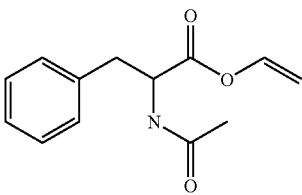 [SMILES: C=COC(=O)C(Cc1ccccc1)NC(C)=O]

Lit.: M. I. Weinhouse, K. D. Janda, "A new methodology for the preparation of vinyl esters", Synthesis 1, 81-83 (1993).
a) Synthesis of N-acetylphenylalanine 2-(phenylseleno)ethyl ester In a 50 ml round bottomed flask, 2.55 g (13.3 mmol) of 1-(3-dimethylamino propyl)-3-ethyl carbodiimide hydrochloride and 1.7 g of (8.2 mmol) phenylalanine were added to a solution of 1.87 g (9.3 mmol) of 2-(phenylseleno)ethanol in 20 ml of THF. The reaction mixture was then stirred for 12 hours at room temperature. The mixture was then diluted with 50 ml of ethyl acetate and extracted with 50 ml of a 0.5 M HCl solution. The organic phase was dried over sodium sulfate, filtered, and the solvent was removed in vacuo. Purification by column chromatography (PE:EE=2:1) yielded 2.9 g (91% of th., 98% of lit.) of a yellowish liquid.

$^1$H-NMR (CDCl$_3$), δ (ppm): 7.3-7.1 (10H, m, Ar—H); 6.62 (1H, d, J=8.7 Hz, NH); 4.64 (1H, m, N—CH); 4.31 (2H, t, O—CH$_2$—); 3.25-3.01 (4H, m, —Ar—CH$_2$—+—Se—CH$_2$—); 1.97 (3H, s, —CH$_3$).

b) Synthesis of N-acetylphenylalanine vinyl ester (PAVE)

To a solution of 2.6 g (6.66 mmol) of N-acetylphenylalanine 2-(phenylseleno)ethyl ester in 20 ml of THF, 8 ml of a 30% H$_2$O$_2$ solution were added dropwise within 10 minutes at 0° C., and the solution was stirred at 0° C. for another 30 minutes. After stirring the mixture for 12 hours at room temperature, it was diluted with 80 ml of CHCl$_3$ and extracted with 3×50 ml of water. The organic phases were then dried over sodium sulfate, and the solvent was removed. The residue was taken up in 70 ml of chloroform and was refluxed for 24 hours. After cooling, the solvent was removed. Flash column—chromatography (PE:EE=3:1) yielded 1.3 g (84% of th., 93% of lit.) of a light-yellow liquid.

$^1$H-NMR (CDCl$_3$), δ (ppm): 7.3-7.1 (6H, m, Ar—H+H$_2$C=CH—); 6.4 (1H, d, J=8.9 Hz, NH); 4.86 (1H, dd, J=13.67/1.51 Hz, —HC=CHH); 4.65 (1H, m, N—CH); 4.54 (1H, dd, J=6.18/1.51 Hz, —HC=CHH); 3.25-3.05 (2H, m, —CH$_2$—); 1.95 (3H, s, —CH$_3$).

Synthesis Example 4

Synthesis of diethylene glycol bis[O—(O'-vinylmaleinoyl)polylactate (DVMPL)

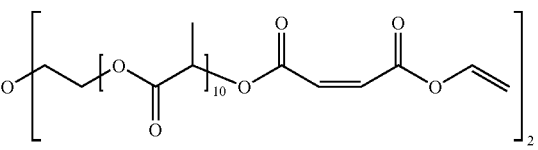

a) Synthesis of diethylene glycol bispolylactate 0.74 g (6.9 mmol) diethylene glycol were stirred overnight with CaCl$_2$ and filtered. The dried alcohol was then precharged into a three-necked flask together with 10 g (69 mmol) of D,L-lactide and heated to 130° C. Once the D,L-lactide had melted, 94 mg (0.2 mmol) Sn-octoate were added as a catalyst, a vacuum was applied, and the mixture was stirred for 6 hours at 130° C. After cooling, the mixture was dissolved in a small amount of CH$_2$Cl$_2$ and precipitated with cold petroleum ether (PE). The supernatant was decanted, and the residue was re-precipitated. 9 g (76% of th.) of a colorless solid could be isolated.

$^1$H-NMR (CDCl$_3$) δ (ppm): 5.13 (20H, m, CH—CO); 4.25 (4H, m, CH$_2$—O); 3.65 (4H, m, CH$_2$—O); 1.55 (60H, m, CH$_3$—C—O).

b) Synthesis of diethylene glycol bis[(O-maleinoyl)polylactate]

8 g (5.2 mmol) of diethylene glycol bispolylactate and 3.74 g (26.1 mmol) of maleic anhydride were dissolved in 100 ml of chloroform and heated to 60° C. for 36 hours. After cooling down to room temperature, the volatile components were removed in vacuo. After reprecipitation from chloroform with petroleum ether, 8.4 g (98% of th.) of a colorless solid were obtained.

$^1$H-NMR (CDCl$_3$) δ (ppm): 6.59 (2H, m, =CH); 6.33 (2H, m, =CH); 5.12 (20H, m, CH—CO); 4.26 (4H, m, CH$_2$—O); 3.64 (4H, m, CH$_2$—O); 1.55 (60H, m, CH$_3$—C—O).

c) Synthesis of diethylene glycol bis[O—(O'-phenylselenoethylmaleinoyl)polylactate]

The synthesis was carried out analogously to synthesis example 3a) using 8.4 g (4.82 mmol) diethylene glycol bis[(O-maleinoyl)polylactate], 2.05 g (10.2 mmol) 2-(phenylseleno)ethanol, 2.61 g (13.6 mmol) 1-(3-dimethylaminopropyl)-3-ethylcarbodiimide hydrochloride, and 2.33 g (19.1 mmol) 4-dimethylaminopyridine in 150 ml of DMF. After reprecipitation from chloroform with PE, 9.8 g (96% of th.) of a yellowish solid were obtained.

$^1$H-NMR (CDCl$_3$) δ (ppm): 7.52 (4H, m, Ar—H); 7.25 (4H, m, Ar—H); 6.51 (2H, d, =CH) 6.48 (2H, d, =CH); 5.12 (20H, m, CH—CO); 4.29 (8H, m, CH$_2$—O+CH$_2$—OCO); 3.64 (4H, m, CH$_2$—O); 3.07 (4H, t, Se—CH$_2$—); 1.53 (m, 60H, CH$_3$—C—O).

d) Synthesis of diethylene glycol bis[O—(O'-vinylmaleinoyl)polylactate (DVMPL)

The synthesis was carried out analogously to synthesis example 3b) using 9.8 g (4.64 mmol) diethylene glycol bis [O—(O'-phenylselenoethylmaleinoyl)polylactate] and 6 ml of a 30% H$_2$O$_2$ solution in 100 ml of THF. Conversion to the vinyl ester was carried out in 150 ml of chloroform. The solution was then concentrated to a volume of 50 ml and the product was precipitated with PE. 7.8 g (95% of th.) of a colorless solid were obtained.

$^1$H-NMR (CDCl$_3$) δ (ppm): 7.26 (2H, m, H$_2$C=CH—); 6.61 (2H, m, =CH); 6.58 (2H, m, =CH); 5.12 (20H, m, CH—CO); 4.85 (2H, m, —HC=CHH); 4.54 (2H, m, —HC=CHH); 4.27 (4H, m, CH$_2$—O); 3.63 (4H, m, CH$_2$—O); 1.55 (60H, m, CH$_3$—C—O).

Synthesis Example 5

Synthesis of (2-oxo-1,3-dioxolane-4-yl)methylmethacrylate (MC)

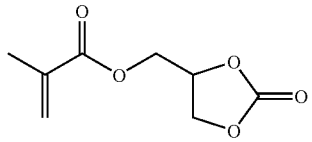

10 ml (78.8 mmol) of triethylamine, 3 g (25.4 mmol) of 4-hydroxymethyl-1,3-dioxolane-2-on were precharged in 35 ml of methylene chloride into a 100 ml flask and flushed with argon. At 0° C., methacrylic acid chloride was slowly added dropwise using a syringe while stirring. The reaction mixture was then stirred for another 2 hours at room temperature. The mixture was extracted with 100 ml of a 1N HCl solution and 100 ml of water, the organic phases were dried over sodium sulfate, filtered, and the solvent was removed in vacuo. Purification by column chromatography (PE:EE=4:1) yielded 3.2 g (68% of th.) of a colorless liquid.

$^1$H-NMR (CDCl$_3$), δ (ppm):6.13 (1H, s, H(H)C=); 5.64 (1H, s, H(H)C=); 5.05-4.87 (1H, m, —CH); 4.62-4.23 (4H, m, 2×—CH$_2$—); 1.93 (3H, s, —CH$_3$).

Synthesis Example 6

Synthesis of frimeric fatty acid trivinyl ester (TFVE)

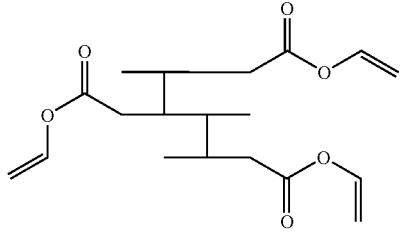 [SMILES: C=COC(=O)CC(C)C(C)C(CC(=O)OC=C)C(C)CC(=O)OC=C]

The synthesis was carried out analogously to synthesis example 1 from trimeric fatty acid (Unidyme 60, Arizona Chemical). Purification by column chromatography on silica gel (PE:EE=5:1) yielded 38.2 g (75% of th.) of the title compound as a yellowish liquid.

R$_f$=0.62 (PE:EE=9:1)

$^1$H-NMR (CDCl$_3$), δ (ppm): 7.30 (3H, dd, J=6.26/14.09 Hz, H$_2$C=CH—O—CO); 4.88 (3H, dd, J=1.47/13.99 Hz, H$_2$C=CH—O—CO, cis); 4.55 (3H, dd, J=1.57/6.26 Hz, H$_2$C=CH—O—CO, trans); 2.39 (7.5H, t, —CH$_2$—COOH); 1.56-0.86 (99.2H, bm, alkyl-H).

IR (ATR, thin film): 2927, 2853, 1750, 1650, 1462, 1141, 954, 870 cm$^{-1}$.

Synthesis Example 7

Synthesis of ω,ω'-3,6,9-trioxaundecanedioic acid divinyl ester (TUVE)

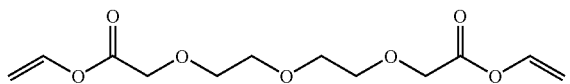 [SMILES: C=COC(=O)COCCOCCOCC(=O)OC=C]

2.94 g (13.4 mmol) of 3,6,9-trioxaundecanedioic acid, 0.46 g (0.7 mmol) of palladium(II)acetate, and 0.08 g potassium hydroxide were precharged in 60 ml vinyl acetate into a 250 ml three-necked flask and stirred under argon atmosphere at 50° C. for 70 hours. After cooling down to room temperature, the obtained solution was diluted with 200 ml of ethyl acetate and extracted two times with 100 ml of water. The organic phase was dried over Na$_2$SO$_4$, and the volatile components were removed using a rotary evaporator. Purification by flash column chromatography on silica gel (PE:EE=1:1) yielded 0.95 g (26% of th.) of a yellow liquid.

R$_f$=0.67 (PE/EA 1:1)

$^1$H-NMR (CDCl$_3$), δ (ppm): 7.29 (2H, dd, J=6.26/13.89 Hz, H$_2$C=CH—O—CO); 4.92 (2H, dd, J=1.76/13.89 Hz, H$_2$C=CH—O—CO, cis); 4.63 (3H, dd, J=1.76/6.26 Hz, H$_2$C=CH—O—CO, trans); 4.24 (4H, s, —O—CH$_2$—COO—); 3.80-3.64 (8H, m, —O—CH$_2$—CH$_2$—O—).

IR (ATR, thin film): 2932, 2882, 1768, 1649, 1240, 1181, 1112, 949, 875 cm$^{-1}$.

Synthesis Example 8

Synthesis of 1,2-ethylene glycol bis(vinyl carbonate) (EGDVC)

1,2-ethanediyl bis(vinyl carbonate), carbonic acid vinyl 2-(vinyloxycarbonyloxy)ethyl ester

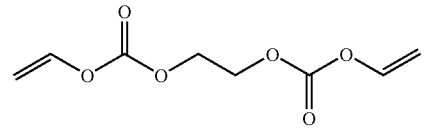

1.5 g (24.2 mmol) of ethylene glycol and 13.3 g (167 mmol) of pyridine were precharged in 50 ml of dichloromethane into a 100 ml single-necked flask. The reaction mixture was then cooled down to 0° C. using an ice bath, and, under an argon atmosphere, 5.56 g (52.2 mmol) of chloroformic acid vinyl ester were added dropwise within 5 minutes using a syringe under stirring. After completion of the addition, the mixture was stirred for another 5 minutes at 0° C. The ice bath was removed, and the reaction mixture was stirred for 1 hour at room temperature. The reaction mixture was then diluted with 100 ml of dichloromethane, and extracted with 150 ml of 1 N hydrochloric acid. The organic phase was then washed with 100 ml of saturated sodium chloride solution and dried over sodium sulfate. The solvent was distilled off in the presence of one spatula tip of hydroquinone. Purification by flash column chromatography (PE:EE=5:1) yielded 4.1 g (84% of th.) of the title compound as a colorless liquid.

$R_f$=0.44 (PE:EE=5:1)

$^1$H-NMR (CDCl$_3$), δ (ppm): 7.06 (2H, dd, J=6.18/13.75 Hz, H$_2$C=CH—O—CO); 4.92 (2H, dd, J=2.37/13.75 Hz, H$_2$C=CH—O—CO); 4.63 (2H, dd, J=2.37/6.18 Hz, H$_2$C=CH—O—CO, trans); 4.43 (4H, s, —CH$_2$—).

Synthesis Example 9

Synthesis of 1,4-butanediol bis(vinyl carbonate) (BDDVC)

Butane-1,4-diyl bis(vinyl carbonate), carbonic acid vinyl 4-(vinyloxycarbonyloxy)butyl ester

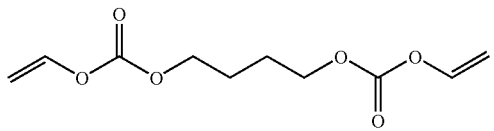 [SMILES: C=COC(=O)OCCCCOC(=O)OC=C]

The synthesis was carried out analogously to synthesis example 8 using 1,4-butanediol and chloroformic acid vinyl ester. Purification by column chromatography on silica gel (PE:EE=3:1) yielded 3.6 g (94% of th.) of the title compound as a colorless liquid.

$R_f$=0.77 (PE:EE=3:1)

$^1$H-NMR (CDCl$_3$), δ (ppm): 7.07 (2H, dd, J=6.16/13.78 Hz, H$_2$C=CH—O—CO); 4.91 (2H, dd, J=2.06/13.78 Hz, H$_2$C=CH—O—CO, cis); 4.57 (2H, dd, J=2.05/6.17 Hz, H$_2$C=CH—O—CO, trans); 4.23 (4H, t, OC—O—CH$_2$—CH$_2$—); 1.81 (4H, m, OC—O—CH$_2$—CH$_2$—).

Elemental analysis (C$_{10}$H$_{14}$O$_6$): calculated C: 52.17, H: 6.13;

found C: 51.78, H: 6.26.

Synthesis Example 10

Synthesis of 1,6-hexanediol bis(vinyl carbonate) (HDDVC)

Hexane-1,6-diyl bis(vinyl carbonate), carbonic acid vinyl 6-(vinyloxycarbonyloxy)hexyl ester

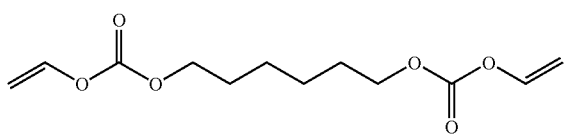 [SMILES: C=COC(=O)OCCCCCCOC(=O)OC=C]

The synthesis was carried out analogously to synthesis example 8 using 1,6-hexanediol and chloroformic acid vinyl ester. Purification by column chromatography on silica gel (PE:EE=5:1) yielded 5.5 g (84% of th.) of the title compound as a colorless liquid.

$R_f$=0.53 (PE:EE=5:1)

$^1$H-NMR (CDCl$_3$), δ (ppm): 7.07 (2H, dd, J=6.16/13.78 Hz, H$_2$C=CH—O—CO); 4.91 (2H, dd, J=2.06/13.78 Hz, H$_2$C=CH—O—CO, cis); 4.57 (2H, dd, J=2.05/6.17 Hz, H$_2$C=CH—O—CO, trans); 4.18 (4H, t, OC—O—CH$_2$—CH$_2$—); 1.70 (4H, m, OC—O—CH$_2$—CH$_2$—); 1.41 (4H, m, —CH$_2$—CH$_2$—CH$_2$—CH$_2$—).

Synthesis Example 11

Synthesis of diethylene glycol bis(vinyl carbonate) (DEGDVC)

3-Oxapentane-1,5-diyl bis(vinyl carbonate), carbonic acid vinyl 2-[2-(vinyloxycarbonyl-oxy)ethoxy]ethyl ester

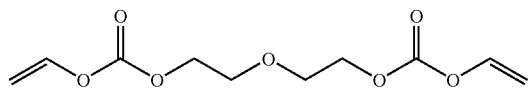 [SMILES: C=COC(=O)OCCOCCOC(=O)OC=C]

The synthesis was carried out analogously to synthesis example 8 using diethylene glycol and chloroformic acid vinyl ester. Purification by column chromatography on silica gel (PE:EE=5:1) yielded 3.3 g (95% of th.) of the title compound as a colorless liquid.

$R_f$=0.42 (PE:EE=3:1)

$^1$H-NMR (CDCl$_3$), δ (ppm): 7.03 (2H, dd, J=6.26/13.88 Hz, H$_2$C=CH—O—CO); 4.87 (2H, dd, J=2.06/13.78 Hz, H$_2$C=CH—O—CO, cis); 4.54 (2H, dd, J=1.96/6.26 Hz, H$_2$C=CH—O—CO, trans); 4.31 (4H, t, (OC—O—CH$_2$—CH$_2$)$_2$—O); 3.71 (4H, t, (OC—O—CH$_2$—CH$_2$)$_2$—O).

Synthesis Example 12

Synthesis of polyethylene glycol(400) bis(vinyl carbonate) (PEGDVC)

Carbonic acid vinyl 2-[ω-(vinyloxycarbonyloxy) polyoxyethylene(400)oxy]ethyl ester

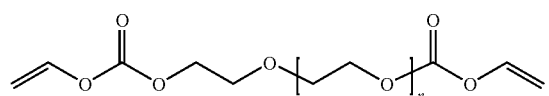

The synthesis was carried out analogously to synthesis example 8 using polyethylene glycol 400 and chloroformic acid vinyl ester. Purification by column chromatography on silica gel (PE:EE=1:2) yielded 2.0 g (93% of th.) of the title compound as a colorless liquid.

$^1$H-NMR (CDCl$_3$), δ (ppm): 7.07 (2H, dd, J=6.26/13.79 Hz, H$_2$C=CH—O—CO); 4.91 (2H, dd, J=1.96/13.79 Hz, H$_2$C=CH—O—CO, cis); 4.57 (2H, dd, J=1.96/6.26 Hz, H$_2$C=CH—O—CO, trans); 4.34 (4H, t, CO—O—CH$_2$—); 3.79-3.56 (26H, m, —CH$_2$—O—).

IR (ATR, thin film): 1758 (C=O), 1650 (C=C), 1241, 1152 cm$^{-1}$.

Synthesis Example 13

Synthesis of diethylene glycol bis[O—(O'-vinyloxy-carbonyl)poly-lactate] (DEG(PLAVC)$_2$)

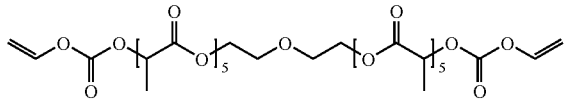

The synthesis was carried out analogously to synthesis example 8 using diethylene glycol bispolylactate and chloroformic acid vinyl ester. The purification was carried out by taking up the mixture in CHCl$_3$ and precipitation in cold PE. 4.1 g (94% of th.) of the title compound were obtained as a colorless, highly viscous oil.

$^1$H-NMR (CDCl$_3$), δ (ppm): 7.04 (2H, dd, J=6.06/13.68 Hz, =CH—O—CO); 5.16 (10H, m, O—CH(CH$_3$)—COO); 4.96 (2H, dd, J=1.94/13.88 Hz, H$_2$C=CH—O—CO, cis); 4.61 (2H, dd, J=1.94/6.06 Hz, H$_2$C=CH—O—CO, trans); 4.40-4.18 (4H, m, OC—O—CH$_2$—CH$_2$—O); 3.72-3.60 (4H, m, OC—O—CH$_2$—CH$_2$—O); 1.70-1.35 (30H, m, O—CH(CH$_3$)—COO).

IR (ATR, thin film): 1750 (C=O), 1652 (C=C), 1263, 1188, 1085 cm$^{-1}$.

Synthesebeispiel 14: Synthesis of 2-cyanoethyl vinyl carbonate (CEVC)

Carbonic acid 2-cyanoethyl vinyl ester

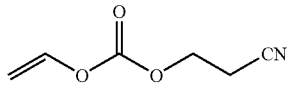

The synthesis was carried out analogously to synthesis example 8 using 2-cyanoethanol(hydroxypropionitrile) and chloroformic acid vinyl ester. Purification by column chromatography on silica gel (PE:EE=3:1) yielded 2.8 g (92% of th.) of the title compound as a colorless liquid.

R$_f$=0.54 (PE:EE=3:1)
$^1$H-NMR (CDCl$_3$), δ (ppm): 7.04 (1H, dd, J=6.16/13.78 Hz, H$_2$C=CH—O—CO); 4.96 (1H, dd, J=2.24/13.78 Hz, H$_2$C=CH—O—CO, cis); 4.64 (1H, dd, J=2.14/6.06 Hz, H$_2$C=CH—O—CO, trans); 4.39 (2H, t, OC—O—CH$_2$); 2.78 (2H, t, CH$_2$—CN).

Elemental analysis (C$_6$H$_7$NO$_3$): calculated C: 51.07, H: 5.00, N: 9.92;
found C: 51.21, H: 4.98, N: 9.73.

Synthesis Example 15

Synthesis of glycerine tris(vinyl carbonate) (GTVC)

Propane-1,2,3-triyltris(vinyl carbonate), carbonic acid 2,3-bis(vinyloxycarbonyloxy)propyl vinyl ester

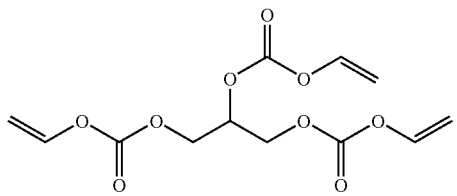 [SMILES: C=COC(=O)OCC(COC(=O)OC=C)OC(=O)OC=C]

The synthesis was carried out analogously to synthesis example 8 using glycerine and chloroformic acid vinyl ester. Purification by column chromatography on silica gel (PE:EE=5:1) yielded 0.8 g (75% of th.) of the title compound as a colorless liquid.

R$_f$=0.64 (PE:EE=3:1)
$^1$H-NMR (CDCl$_3$), δ (ppm): 7.04 (3H, dd, J=6.16/13.78 Hz, H$_2$C=CH—O—CO); 5.21 (1H, m, (OC—O—H$_2$C)$_2$CH—O—CO); 4.94 (3H, dd, J=2.67/11.73 Hz, H$_2$C=CH—O—CO, cis); 4.62 (3H, dd, J=2.34/6.24 Hz, H$_2$C=CH—O—CO, trans); 4.45 (4H, m, (OC—O—H$_2$C)$_2$—CH—O—CO).

Synthesis Example 16

Synthesis of ethyl vinyl carbonate (EVC)

Carbonic acid ethyl vinyl ester

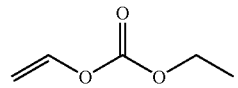

The synthesis was carried out analogously to synthesis example 8 using ethanol and chloroformic acid vinyl ester. Purification by column chromatography on silica gel (PE:EE=5:1) yielded 1.3 g (83% of th.) of the title compound as a colorless liquid.

R$_f$=0.58 (PE:EE=3:1)
$^1$H-NMR (CDCl$_3$), δ (ppm): 7.06 (1H, dd, J=6.26/13.88 Hz, H$_2$C=CH—O—CO); 4.88 (1H, dd, J=1.96/13.88 Hz, H$_2$C=CH—O—CO, cis); 4.54 (1H, dd, J=1.96/6.06 Hz, H$_2$C=CH—O—CO, trans); 4.24 (2H, q, OC—O—CH$_2$—CH$_3$); 1.31 (3H, t, OC—O—CH$_2$—CH$_3$).

Synthesis Example 17

Synthesis of Ricinus Oil tris(vinyl carbonate) (RiTVC)

Mainly (about 80%): propane-1,2,3-triyltris[(R)—(Z)-12-vinyloxycarbonyloxy-9-octa-decenoate]

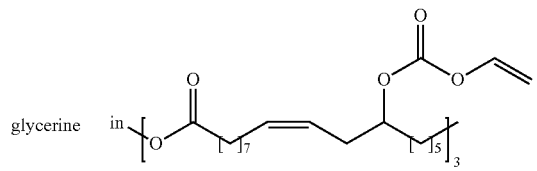

The synthesis was carried out analogously to synthesis example 8 using ricinus oil and chloroformic acid vinyl ester. Purification by column chromatography on silica gel (PE:EE=5:1) yielded 1.5 g (53% of th.) of a colorless, viscous liquid.

$^1$H-NMR (CDCl$_3$), δ (ppm): 7.08 (3H, dd, J=6.26/13.88 Hz, H$_2$C=CH—O—CO); 5.55-5.22 (8H, m, —CH$_2$—CH=CH—CH$_2$ and CH$_2$)$_2$—CH—O—CO); 4.88 (3H, dd, J=1,76/13.88 Hz, H$_2$C=CH—O—CO, cis); 4.75 (3H, quin, CH$_2$—CHO—CH$_2$); 4.55 (3H, dd, J=1.76/6.06 Hz, H$_2$C=CH—O—CO, trans); 4.23 (2H, dd, CO—O—CH$_2$); 4.19 (2H, dd, CO—O—CH$_2$); 2.45-2.22 (12H, m, OOC—C H₂—CH₂ and HC=CH—CH₂—COH); 2.12-1.95 (6H, m); 1.72-1.10 (60H, m); 1.02-0.80 (9H, m).

IR (ATR, thin film): 1751 (C=O), 1650 (C=C), 1252, 1158 cm⁻¹.

Synthesis Example 18

Synthesis of Hydrated Ricinus Oil tris(vinyl carbonate) (H RiTVC)

Mainly (about 80%): Propane-1,2,3-triyltris[(R)—(Z)-12-vinyloxycarbonyloxyocta-decanoate]

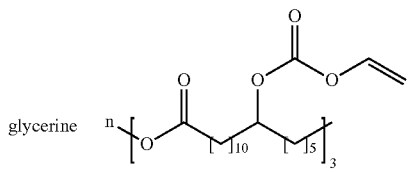

The synthesis was carried out analogously to synthesis example 8 using hydrated ricinus oil (Loxiol G 15, Oleo Chemicals) and chloroformic acid vinyl ester. Purification by column chromatography on silica gel (PE:EE=5:1) yielded 0.77 g (77% of th.) of a colorless, viscous liqiuid.

¹H-NMR (CDCl₃), δ (ppm): 7.10 (3H, dd, J=6.16/13.79 Hz, H₂C=CH—O—CO); 5.39-5.20 (8H, m, —CH₂—CH=CH—CH₂ [6H] and (CH₂)₂—CH—O—CO [2H]); 4.90 (3H, dd, J=1.86/13.79 Hz, H₂C=CH—O—CO, cis); 4.75 (1H, m, CH₂—CHO—CH₂); 4.55 (3H, dd, J=1.86/6.16 Hz, H₂C=CH—O—CO, trans); 4.29 (2H, dd, OCO—CH₂—COH); 4.14 (2H, dd, OCO—CH₂—COH); 2.45-2.22 (12H, m, OOC—CH₂—CH₂ [6H] and HC=CH—CH₂—COH [6H]); 2.31 (6H, t); 1.70-1.50 (18H, m); 1.50-1.20 (81H, m); 1.08-0.82 (14H, m).

IR (ATR, thin film): 2932, 2858, 1753, 1462, 1250, 1156, 949, 865 cm⁻¹.

Synthesis Example 19

Synthesis of N,N'-dimethyl-1,2-ethylenediamine bis(vinyl carbamate) (DMEDDVCA)

N,N'-dimethyl-N,N'-ethane-1,2-diyl bis(carbamic acid), N-methyl-N-2-[N'-methyl-N'-(vinyloxycarbonyl)amino]ethylcarbamic acid vinyl ester

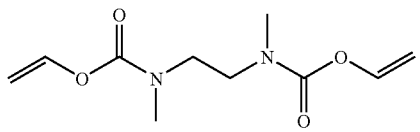 [SMILES: C=COC(=O)N(C)CCN(C)C(=O)OC=C]

The synthesis was carried out analogously to synthesis example 8 using N,N'-dimethyl-1,2-ethylenediamin and chloroformic vinyl ester. Purification by column chromatography on silica gel (PE:EE=1:1) yielded 3.1 g (96% of th.) of the title compound as a colorless liquid.

R_f=0.47 (PE:EE=1:1)

¹H-NMR (CDCl₃), δ (ppm): 7.17 (2H, m, H₂C=CH—O—CO); 4.75 (2H, m, H₂C=CH—O—CO, cis); 4.42 (2H, m, H₂C=CH—O—CO, trans); 3.47 (4H, s, N—CH₂); 2.98 (6H, s, N—CH₃).

Elemental analysis (C₁₀H₁₆N₂O₄): calculated C: 52.62, H: 7.07, N: 12.27;

found C: 52.34, H: 6.99, N: 12.10.

Synthesis Example 20

Synthesis of piperazine bis(vinyl carbamate) (PDVCA)

Diethylenediamine bis(vinyl carbamate), N,N'-bis(vinyloxycarbonyl)hexahydro-1,4-diazine

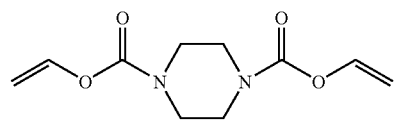 [SMILES: C=COC(=O)N1CCN(C(=O)OC=C)CC1]

The synthesis was carried out analogously to synthesis example 8 using piperidine and chloroformic acid vinyl ester. Purification by column chromatography on silica gel (PE:EE=1:1) yielded 1.2 g (91% of th.) of the title compound as a colorless liquid.

R_f=0.70 (PE:EE=1:1)

¹H-NMR (CDCl₃), δ (ppm): 7.21 (2H, dd, J=6.36/13.98 Hz, H₂C=CH—O—CO); 4.81 (2H, dd, J=1.66/11.73 Hz, H₂C=CH—O—CO, cis); 4.50 (2H, dd, J=1.76/6.26, H₂C=CH—O—CO, trans); 3.56 (8H, s, CH₂—CH₂).

Synthesis Example 21

Synthesis of 3,3'-ethylenedioxy bis(propylamine)divinyl carbamate (Jeffamine bis(vinyl carbamate), JAVM)

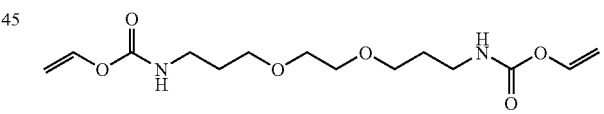

The synthesis was carried out analogously to synthesis example 8 using 3,3'-ethylene-dioxy bis(propylamine) and chloroformic acid vinyl ester. Purification by column chromatography on silica gel (PE:EE=1:1) yielded 1.03 g (72% of th.) of the title compound as a colorless liquid.

R_f=0.43 (PE:EE=1:1)

¹H-NMR (CDCl₃), δ (ppm): 7.20 (2H, dd, J=6.36/13.99 Hz, H₂C=CH—O—CO); 5.93-5.73 (0.6H, bs, —OC—NH—CH₂—); 5.65-5.39 (1.4H, bs, —OC—NH—CH₂—); 4.69 (2H, dd, J=1,37/14.09 Hz, H₂C=CH—O—CO, cis); 4.40 (2H, dd, J=1.08/6.36 Hz, H₂C=CH—O—CO, trans); 3.66-3.46 (8H, m, —CH₂—O—CH₂—CH₂—O—CH₂—); 3.35 (4H, q, —CH₂—CH₂—NH—CO—); 1.82 (4H, quin, —O—CH₂—CH₂—CH₂—NH—).

IR (ATR, thin film): 3331, 2932, 2872, 1718, 1649, 1526, 1240, 1166, 1101, 954, 860 cm⁻¹.

Synthesis Example 22

Synthesis of bis[ω-aminopolyethylene glycol(500)]amine tris(vinyl carbamate) (EAVM)

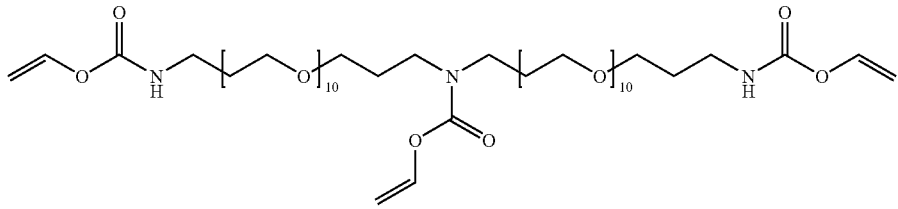

The synthesis was carried out analogously to synthesis example 8 using bis[ω-amino-polyethylene glycol(500))amine (Jeffamine EDH-176, Huntsman) and chloroformic acid vinyl ester. Purification by column chromatography on silica gel (PE:EE=1:1) yielded 2.02 g (86% of th.) of the title compound as a colorless liquid.

$^1$H-NMR (CDCl$_3$), δ (ppm): 7.14 (2H, dd, J=6.36/13.99 Hz, H$_2$C=CH—O—CO—NH); 7.13 (1H, dd, J=6.36/13.99 Hz, H$_2$C=CH—O—CO—N(CH$_2$)$_2$); 5.82-5.62 (2H, bs, —OC—NH—CH$_2$—); 4.70 (1H, dd, J=1.47/13.99 Hz, H$_2$C=CH—O—CO—N(CH$_2$)$_2$, cis); 4.65 (2H, dd, J=1.27/13.99 Hz, H$_2$C=CH—O—CO—NH, cis); 4.39 (1H, dd, J=1.37/6.26 Hz, H$_2$C=CH—O—CO—N(CH$_2$)$_2$, trans); 4.35 (2H, dd, J=1.37/6.26 Hz, H$_2$C=CH—O—CO—NH, trans); 3.72-3.40 (92H, m, —CH$_2$—O—CH$_2$—CH$_2$—O—CH$_2$—); 3.37-3.30 (4H, m, —CH$_2$—CH$_2$—NH—CO—).

IR (ATR, thin film): 3336, 2872, 1743, 1718, 1649, 1526, 1245, 1101, 949, 860 cm$^{-1}$.

Synthesis Example 23

Synthesis of Sarcosine methylester vinyl carbamate (SMEVCA)

N-methyl-N-(vinyloxycarbonyl)glycine methyl ester, N-(methoxycarbonylmethyl)-N-methylcarbamic acid vinyl ester

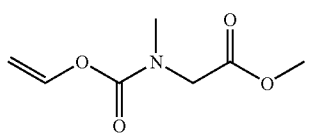

The synthesis was carried out analogously to synthesis example 8 using sarcosine and chloroformic acid vinyl ester. Purification by column chromatography on silica gel (PE:EE=1:1) yielded 1.9 g (96% of th.) of the title compound as a colorless liquid.

R$_f$=0.57 (PE:EE=1:1)

$^1$H-NMR (CDCl$_3$), δ (ppm): 7.12 (1H, m, H$_2$C=CH—O—CO); 4.76 (1H, m, H$_2$C=CH—O—CO, cis); 4.44 (1H, m, H$_2$C=CH—O—CO, trans); 4.03 (2H, s, N—CH$_2$—COO); 4.03 (3H, s, CO—O—CH$_3$); 2.99 (3H, s, N—CH$_3$).

Elemental analysis (C$_7$H$_{11}$NO$_4$): calculated C: 48.55, H: 6.40, N: 8.09;
found C: 48.51, H: 6.56, N: 8.02.

Synthesis Example 24

Synthesis of N,O-Bis(vinyloxycarbonyl)-N-methyl hydroxylamine (MHADVC)

N-methyl-N-(vinyloxycarbonyloxy)carbamic acid vinyl ester

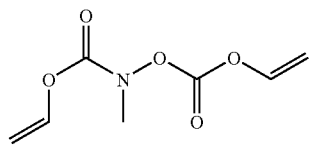

The synthesis was carried out analogously to synthesis example 8 using N-methyl hydroxylamine and chloroformic acid vinyl ester. Purification by column chromatography on silica gel (PE:EE=6:1) yielded 1.4 g (86% of th.) of the title compound as a colorless liquid.

R$_f$=0.36 (PE:EE=6:1)

$^1$H-NMR (CDCl$_3$), δ (ppm): 7.17-7.00 (2H, m, CH$_2$=CH—O—CO); 5.09-5.1 (1H, dd, J=2.4/13.7 Hz, CH$_2$=CH—O—CO—N, cis); 4.94-4.86 (1H, dd, J=2.0/13.9 Hz, CH$_2$=CH—O—CO—O, cis); 4.75-4.71 (1H, dd, J=2.6/6.07 Hz, CH$_2$=CH—O—CO—N, trans); 4.62-4.58 (1H, dd, J=2.1/6.2 Hz, CH$_2$=CH—O—CO—O, trans); 3.75 (3H, s, —NCH$_3$).

Elemental analysis (C$_7$H$_9$NO$_5$): calculated C: 44.92, H: 4.85, N: 7.48;
found C: 44.54, H: 5.06, N: 7.24.

Synthesis Example 25

Synthesis of N-methoxy vinyl carbamate (MVCA)

N-Methoxycarbamic acid vinyl ester

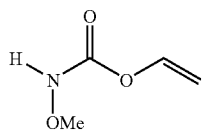

The synthesis was carried out analogously to synthesis example 8 using O-methyl hydroxylamine and chloroformic acid vinyl ester. Purification by column chromatography on silica gel (PE:EE=8:1) yielded 0.9 g (79% of th.) of the title compound as a colorless liquid.

R$_f$=0.18 (PE:EE=8:1)

$^1$H-NMR (CDCl$_3$), δ (ppm): 7.22-7.112 (1H, dd, J=6.1/13.7 Hz, H$_2$C=CH—O—CO); 4.88-4.80 (1H, dd, J=2.0/13.7 Hz, H$_2$C=CH—O—CO, cis); 4.57-4.53 (1H, dd, J=1.9/6.3 Hz, H$_2$C=CH—O—CO, trans); 3.76 (3H, s, O—CH$_3$).

Elemental analysis (C$_4$H$_7$NO$_3$): calculated C: 41.03, H: 6.03, N: 11.96;

found C: 41.25, H: 6.16, N: 11.74.

Synthesis Example 26

Synthesis of N-acryloyl-N-methoxy vinyl carbamate (AMVCA)

N-Methoxy-N-propenoylcarbamic acid vinyl ester

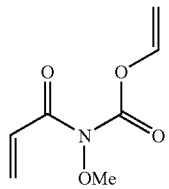

The synthesis was carried out analogously to synthesis example 8 using N-methoxy-acrylamide and chloroformic acid vinyl ester. Purification by column chromatography on silica gel (PE:EE=9:1) yielded 1.6 g (91% of th.) of the title compound as a colorless liquid.

R$_f$=0.34 (PE:EE=9:1)

$^1$H-NMR (CDCl$_3$), δ (ppm): 7.12-7.02 (1H, dd, J=6.3/13.8 Hz, CH$_2$=CH—O—CO); 6.29-6.21 (1H, dd, J=11.0/17.5 Hz, CH$_2$—CH—CO—N); 5.80-5.71 (1H, dd, J=0.5/17.5 Hz, CH$_2$=CH—CO—N, cis); 5.58-5.25 (1H, dd, J=0.5/11.3 Hz, CH$_2$=CH—CO—N, trans); 5.07-4.99 (1H, dd, J=2.3/13.7 Hz, CH$_2$=CH—O—CO, cis); 4.71-4.67 (1H, dd, J=2.3/6.1 Hz, CH$_2$=CH—O—CO, trans); 3.90 (3H, s, —OCH$_3$).

Elemental analysis (C$_7$H$_9$NO$_3$): calculated C: 49.12, H: 5.30, N: 8.18;

found C: 49.08, H: 5.38, N: 8.22.

Synthesis Example 27

Synthesis of vinyloxycarbonyl phosphonic acid diethyl ester (VCPDE)

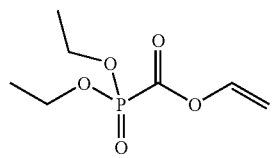

2.0 g (19 mmol) of chloroformic acid vinyl ester were precharged into a 50 ml two-necked flask, and, while stirring at 0° C., 3.13 g (19 mmol) of triethyl phosphite were slowly added dropwise. After completion of the addition, the reaction mixture was stirred for further 2 hours at room temperature. For complete removal of the ethyl chloride formed during the reaction, the solution was heated to 40° C. for 30 minutes. Purification by vacuum destillation yielded 2.5 g (64% of th.) of the title compound as a colorless liquid.

Bp.: 125-128° C./8 mbar

R$_f$=0.35 (PE:EE=1:1)

$^1$H-NMR (CDCl$_3$), δ (ppm): 7.01-6.99 (1H, dd, J=0.7/6.3 Hz, H$_2$C=CH—O—CO); 4.88-4.79 (1H, m, H$_2$C=CH—O—CO, cis); 4.55-4.48 (1H, m, H$_2$C=CH—O—CO, trans); 4.12-3.97 (4H, m, O—CH$_2$); 1.17-1.09 (6H, m, —CH$_3$).

Elemental analysis (C$_7$H$_{13}$O$_5$P): calculated C: 40.39, H: 6.30, P: 14.88;

found C: 40.60, H: 6.24, P: 14.71.

Synthesis Example 28

Synthesis of 2-(diethoxyphosphoryloxy)ethylamine vinyl carbamate (EPEVC)

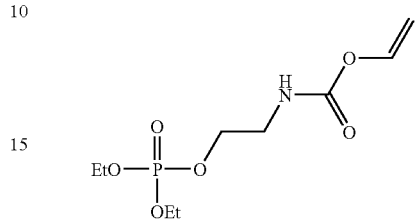

0.81 ml of triethylamine (5.8 mmol) were precharged in 10 ml of abs. THF, and 0.76 g of 2-hydroxyvinyl carbamate (5.8 mmol) were added. The reaction solution was then cooled to −78° C., and 0.83 ml of diethylchlorophosphonite (5.8 mmol) in 4 ml of THF were added dropwise. After completion of the addition, the reaction mixture was stirred for 12 hours at room temperature. A white solid was filtered off, and the residue was washed with a 5% aqueous solution of sodium hydrogen carbonate (3×10 ml). The organic phase was then dried over sodium sulfate. After filtering off the siccative, the solvent was removed on a rotary evaporator. The crude product was purified by column chromatography on silica gel (PE:EE=1:5). 0.39 g (25% of th.) of the title compound were obtained as a colorless oil.

R$_f$=0.28 (PE:EE=1:5)

$^1$H-NMR (CDCl$_3$), δ (ppm): 7.11-7.19 (1H, dd, J=6.4/14.0 Hz, CH$_2$=CH); 5.69 (1H, s, N—H); 4.68-4.74 (1H, dd, J=1.3/14.0 Hz, CH$_2$=CH, trans); 4.39-4.42 (1H, dd, J=1.2/6.3 Hz, CH$_2$=CH, cis); 4.04-4.16 (6H, m, CH$_2$—CH$_3$, P—OCH$_2$); 3.45-3.51 (2H, m, CH$_2$NH); 1.29-1.35 (6H, m, CH$_2$—CH$_3$).

Elemental analysis (C$_9$H$_{18}$NO$_6$P:): calculated C: 40.42, H: 6.74, N: 5.24;

found C: 40.10, H: 6.61, N: 4.99.

Synthesis Example 29

Synthesis of ethyl bis[2-(vinyloxycarbonylamino)ethyl]phosphate (EBVCAEP)

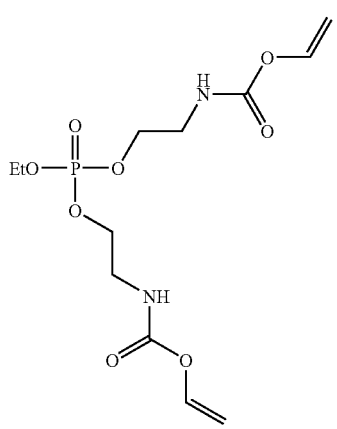 [SMILES: C=COC(=O)NCCOP(=O)(OCC)OCCNC(=O)OC=C]

The synthesis was carried out analogously to synthesis example 28 using 2 equivalents 2-hydroxyethylamine vinyl carbamate and 1 equivalent dichloroethyl phosphinate. The crude product was purified by column chromatography on silica gel (PE:EE=1:5). 1.05 g (43% of th.) of the title compound were obtained as a colorless, highly viscous oil.

$R_f$=0.23 (PE:EE=1:5)

$^1$H-NMR (CDCl$_3$), δ (ppm): 7.11-7.21 (2H, dd, J=6.3/14.3 Hz, CH$_2$=C$\underline{H}$); 5.76 (2H, s, N—H); 4.69-4.76 (2H, dd, J=1.4/14.1 Hz, C$\underline{H}_2$=CH, trans); 4.40-4.44 (2H, dd, J=1.6/6.3 Hz, C$\underline{H}_2$=CH, cis); 4.04-4.19 (6H, m, C$\underline{H}_2$—CH$_3$, POC$\underline{H}_2$—CH$_2$); 3.44-3.51 (4H, m, C$\underline{H}_2$NH); 1.26-1.35 (3H, m, CH$_2$—C$\underline{H}_3$).

Elemental analysis (C$_{12}$H$_{21}$N$_2$O$_8$P:): calculated C: 40.91, H: 6.01, N: 7.95;

found C: 40.63, H: 5.70, N: 7.90.

Synthesis Example 30

Synthesis of diethyl vinyl phosphate (DEVP)

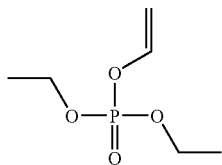

10 ml of N-butyllithium solution (2.1 M solution in hexane) were added dropwise to 50 ml of abs. THF under an argon atmosphere at 0° C. The solution was stirred for 30 minutes at 0° C. and for 15 hours at room temperature, then added to 3.01 ml diethyl chlorophosphonate (20 mmol) at −76° C. and stirred for 1 h at 0° C., then for 16 hours at room temperature. A white solid was filtered off, and the solvent was removed on a rotary evaporator. The slightly yellowish crude product was purified by column chromatography on silica gel (PE:EE=4:1). 2.2 g (60% of th.) of the title compound were obtained as a yellowish liquid.

$R_f$=0.48 (PE:EE=4:1)

$^1$H-NMR (CDCl$_3$), δ (ppm): 6.51-6.61 (1H, dd, J=6.3/12.6 Hz, CH$_2$=C$\underline{H}$); 4.85-4.91 (1H, dd, J=1.2/12.6 Hz, C$\underline{H}_2$=CH, trans); 4.53-4.57 (1H, dd, J=1.2/6.3 Hz, C$\underline{H}_2$=CH, cis); 4.09-4.21 (4H, m, C$\underline{H}_2$—CH$_3$); 1.29-1.37 (6H, m, CH$_2$—C$\underline{H}_3$).

Synthesis Example 31

Synthesis of divinyl ethyl phosphate (DVEP)

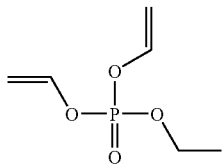

The synthesis was carried out analogously to synthesis example 30 using n-butyllithium solution (2.1 M solution in hexane)/THF and dichloroethyl phosphinate. The dark yellow crude product was purified by column chromatography on silica gel (PE:EE=3:1). 1.9 g (36% of th.) of the title compound were obtained as a yellow liquid.

$R_f$=0.42 (PE: EE=3:1)

$^1$H-NMR (CDCl$_3$), δ (ppm): 6.48-6.65 (2H, dd, J=1.4/6.6 Hz, CH$_2$=C$\underline{H}$); 4.87-5.01 (2H, dd, J=1.1/13.5 Hz, C$\underline{H}_2$=CH, trans); 4.57-4.68 (2H, m, C$\underline{H}_2$=CH, cis); 4.14-4.32 (2H, m, C$\underline{H}_2$—CH$_3$); 1.30-1.45 (3H, m, CH$_2$—C$\underline{H}_3$).

Elemental analysis (C$_6$H$_{11}$O$_4$P): calculated C: 40.46, H: 6.22;

found C: 40.68, H: 6.11.

Synthesis Example 32

Synthesis of trivinyl phosphate (TVP)

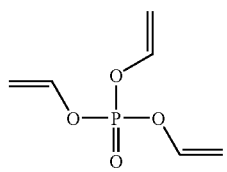

The synthesis was carried out analogously to synthesis example 30 using n-butyllithium solution (2.1 M solution in hexane)/THF and phosphorylchloride. The orange-yellow crude product was purified by column chromatography on silica gel (PE:EE=5:1). Es wurden 1.0 g (26% of th.) of the title compound were obtained as a dark yellow liquid.

$R_f$=0.43 (PE:EE=5:1)

$^1$H-NMR (CDCl$_3$), δ (ppm): 6.46-6.66 (3H, m, CH$_2$=C$\underline{H}$); 4.86-5.09 (3H, m, C$\underline{H}_2$=CH, trans); 4.57-4.77 (3H, m, C$\underline{H}_2$=CH, cis).

Synthesis of Higher Molecular Weight Compounds

The synthesis of compounds in which R$^1$ is an n-valent radical of a biodegradable, biocompatible oligomer or polymer, e.g. vinyl esters of natural products, is carried out analogously to the preparation of the corresponding vinyl esters, vinyl carbonates, and vinyl carbamates.

OH— group-containing polymers, e.g. polysaccharids such as glycogen, amylose, cellulose, or hydroxyethyl cellulose, may, for example, be reacted with chloroformic acid vinyl ester in a suitable solvent such as DMA/LiCl. Analogously to the synthesis of the polylactate block co-polymers in synthesis example 6, all OH-terminated polyesters (e.g. OH-terminated polyglycolic acid) and polyethers (e.g. PEG 2000) may be reacted to yield the corresponding carbonates.

The free amino groups on the lysine units of gelatine spontaneously react with chloroformic acid vinyl ester to yield the corresponding carbamates. Analogously thereto, various further polypeptides and proteins may be converted. Chitosan can be reacted, too, in which case, if the equivalents of chloroformic acid vinyl ester are appropriately selected, the amino groups react selectively before the OH-groups.

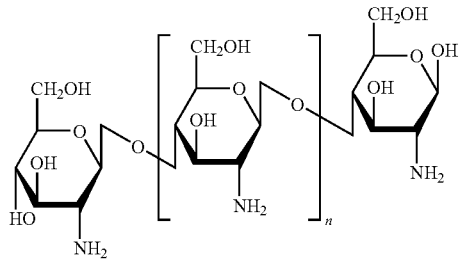

Chitosan

Chitosan may also be used for the preparation of vinyl esters. To this end, for example, the free amino groups are reacted with vinyl acrylate, said groups reacting with the acrylate double bound in a Michael reaction. Another possibility for obtaining vinyl esters consists in the Pd(II)-catalyzed reaction of carboxyethyl cellulose, analogously to the preparation of TUVE from trioxaundecanedioic acid in synthesis example 7.

Vinyl esters according to the invention on a sulfur basis may be obtained according to any of the above procedures, e.g. from thiols, the reaction of the thiol group, e.g. of a polypeptide having cystein residues, with chloroformic acid vinyl ester again being the easiest way.

Further, the free P—OH group of phospholipids such as phosphatidylcholines can at first be reacted under mild conditions with oxalyl chloride in order to obtain the respective acid chloride. The desired vinyl ester of the phospholipid may then be obtained by a reaction carried out analogously to the examples 30 and 31.

Thus, a high number of polysaccharides, polypeptides, polyamides, polyesters, polycarbonates, polyethers, and fatty acid derivatives having functionalities such as hydroxy, thiol- and/or amino groups, which can easily be reacted, can easily be converted into the respective vinyl esters and thereafter into a polymerizable composition of the present invention, in order to yield desired biodegradable, biocompatible, crosslinked polymers, which are, for example, suited for being used as bone substitute materials or tissue supportive/substitute materials.

The solubility of the starting polymer is usually significantly improved by converting it into the corresponding vinyl ester. However, almost only solids are thus obtainable. Especially in these cases, liquid co-monomers and/or solvents in more or less high amounts are required for the use as a photopolymerizable formulation. Less than 5% (for example, 1%) solutions of monomers in the respective solvent are also possible, but are not preferred according to the invention, as they provide for low polymerization rates and often require high amounts of energy for the subsequent removal of the solvent. Molding these products using rapid prototyping procedures would be difficult, too. There is, of course, the possibility to increase the viscosity of heavily diluted monomer solutions by means of thickening agents to practical values, which, however, is not preferred, either.

Thus, the following examples of the present invention describe preferred embodiments of the compositions of the invention which only contain viscous/liquid vinyl ester monomers and initiators. The type and amount of solvents and additives, which may be optionally added and which have already been described in detail above, may be selected by the average artisan without undue experimentation.

Examples 1 to 50

Preparation of Compositions of the Invention

Mono- and difunctional vinyl esters were used as monomers of formulas (I) to (III)—in two cases in combination with the co-monomer (2-oxo-1,3-dioxolan-4-yl)methyl meth-acrylate (MC) prepared in synthesis example 5—and were mixed with one of the following UV photoinitiators (A) to (C) in order to yield compositions of the invention:

Initiator A: 0.5% by weight of Irgacure 819 (Ciba)
Intiator B: 1% by weight of camphor quinone and 4-dimethylaminobenzoic acid ethyl ester (CC/DMAB) at a molar ratio of 1:1
Initiator C: 2% by weight of Darocur 1173 (Ciba)

In example 19, the surface of a cured sample consisting of an AVE/MC co-polymer was modified in the following way using alkaline phosphatase (ALP) as an example of an enzyme as a bioactive agent:

A small polymer plate having a diameter of 1.3 cm was immersed in 3 ml of an ALP solution (2 mg/ml) and was agitated for 16 hours in 0.05 M Tris-HCl buffer at pH 8 and 4° C. The plate was washed several times with the buffer solution, and free, unreacted carbonate MC was reacted with ethanol amine.

A general overview of enzyme immobilization on polymers having cyclic carbonates on their surfaces can be found in D. C. Webster, "Cyclic carbonate functional polymers and their applications", Progress in Organic Coatings 47(1), 77-86 (2003).

In this way, in the following examples 1 to 50, the respective compositions of the invention E1 to E50 were obtained.

| | | |
|---|---|---|
| Example 1: decanoic acid vinyl ester, DVE | n = 1 | Initiator A |
| Example 2: hexanoic acid vinyl ester, HVE | n = 1 | Initiator A |
| Example 3: N-acetylphenylalanin vinyl ester, PAVE | n = 1 | Initiator A |
| Example 4: adipic acid divinyl ester, AVE | n = 2 | Initiator A |
| Example 5: sebacic acid divinyl ester, SEVE | n = 2 | Initiator A |
| Example 6: octanedioic acid divinyl ester, KVE | n = 2 | Initiator B |
| Example 7: adipic acid divinyl ester, AVE | n = 2 | Initiator B |
| Example 8: sebacic acid divinyl ester, SEVE | n = 2 | Initiator B |
| Example 9: octanedioic acid divinyl ester, KVE | n = 2 | Initiator B |
| Example 10: AVE:HVE = 1:1 | | Initiator B |
| Example 11: AVE:HVE = 3:1 | | Initiator B |
| Example 12: AVE:DVE = 1:1 | | Initiator B |
| Example 13: AVE:DVE = 3:1 | | Initiator B |
| Example 14: AVE:PAVE = 1:1 | | Initiator B |
| Example 15: AVE:PAVE = 3:1 | | Initiator B |
| Example 16: AVE:DVMPL = 1:1 | | Initiator B |
| Example 17: AVE:DVMPL = 3:1 | | Initiator B |
| Example 18: AVE:MC = 20:1 | | Initiator B |
| Example 19: AVE:MC = 20:1 plus surface modification | | Initiator B |
| Example 20: trimeric fatty acid trivinyl ester, TFVE | n = 3 | Initiator A |
| Example 21: trioxaundecanedioic acid divinyl ester, TUVE | n = 2 | Initiator A |
| Example 22: ethylene glycol bis(vinyl carbonate), EGDVC | n = 2 | Initiator A |
| Example 23: butanediol bis(vinyl carbonate), BDDVC | n = 2 | Initiator A |
| Example 24: hexanediol bis(vinyl carbonate), HDDVC | n = 2 | Initiator A |
| Example 25: glycerine tris(vinyl carbonate), GTVC | n = 3 | Initiator A |
| Example 26: diethylene glycol bis(vinyl carbonate), DEGDVC | n = 2 | Initiator A |
| Example 27: polyethylene glycol bis(vinyl carbonate), PEGDVC | n = 2 | Initiator A |
| Example 28: 2-cyanoethyl vinyl carbonate, CEVC | n = 1 | Initiator A |
| Example 29: ethyl vinyl carbonate, EVC | n = 1 | Initiator A |

-continued

| | | |
|---|---|---|
| Example 30: ricinus oil tris(vinyl carbonate), RiTVC | n = 3 | Initiator A |
| Example 31: hydrated ricinus oil tris(vinyl carbonate), HRiTVC | n = 3 | Initiator A |
| Example 32: diethylene glycol bis[O-(O'-vinyloxycarbonyl)polylactate], DEG(PLAVC)$_2$ | n = 2 | Initiator A |
| Example 33: N,N'-dimethylethylenediamine bis(vinyl carbamate), DMEDDVCA | n = 2 | Initiator A |
| Example 34: piperazine bis(vinyl carbamate), PDVCA | n = 2 | Initiator A |
| Example 35: ethylenedioxy bis(propylamine) divinyl carbamate, JAVM | n = 2 | Initiator A |
| Example 36: bis[aminopolyethylene glycol(500)]amine trivinyl carbamate, EAVM | n = 3 | Initiator A |
| Example 37: sarcosine methyl ester vinyl carbamate, SMEVCA | n = 1 | Initiator A |
| Example 38: N,O-bis(vinyloxycarbonyl)-N-methylhydroxylamine, MHADVC | n = 2 | Initiator C |
| Example 39: N-methoxy vinyl carbamate, MVCA | n = 1 | Initiator C |
| Example 40: N-acryloyl-N-methoxy vinyl carbamate, AMVCA | n = 1 | Initiator C |
| Example 41: vinyloxycarbonyl phosphonic acid diethyl ester, VCPDE | n = 1 | Initiator C |
| Example 42: EGDVC:CEVC = 5:1 | | Initiator A |
| Example 43: EGDVC:EVC = 5:1 | | Initiator A |
| Example 44: DMEDDVCA:PDVCA = 5:1 | | Initiator A |
| Example 45: DMEDDVCA:SMEVCA = 5:1 | | Initiator A |
| Example 46: 2-(diethoxyphosphoryloxy)ethylamine vinyl carbamate, EPEVC | n = 1 | Initiator A |
| Example 47: ethyl bis[2-(vinyloxycarbonylamino)ethyl] phosphate, EBVCAEP | n = 2 | Initiator A |
| Example 48: diethyl vinyl phosphate, DEVP | n = 1 | Initiator A |
| Example 49: divinyl ethyl phosphate, DVEP | n = 2 | Initiator A |
| Example 50: trivinyl phosphate, TVP | n = 3 | Initiator A |

Comparative Examples 1 to 8

Preparation of Reference Compositions

Instead of the vinyl ester monomers of the present invention, other photopolymerizable monomers were mixed with initiators analogously to the above examples in order to obtain the reference compositions C1 to C8 representing the state of the art as comparative examples.

| | |
|---|---|
| Comparative example 1: 1,6-hexanediol diacrylate, HDDA | Initiator A |
| Comparative example 2: hrimethylolpropane triacrylate, TTA | Initiator A |
| Comparative example 3: ethoxylated TTA, MG 1200, ETA | Initiator A |
| Comparative example 4: polyethylene glycol diacrylate, MG 800, PEG-DA | Initiator A |
| Comparative example 5: 1,4-butanediol dimethacrylate, BDMA | Initiator A |
| Comparative example 6: 1,6-hexanediol diacrylate, HDDA | Initiator B |
| Comparative example 7: polyethylene glycol diacrylate, MG 800, PEG-DA | Initiator B |
| Comparative example 8: TTA:ETA = 1:1 | Initiator B |

Curing Tests

For the curing tests, the compositions of the invention E1 to E6, E20 to E41, and E46 to E50, which were obtained as described above, and the reference compositions C1 to C5 were used. For photo-DSC measurements, approximately 5 mg of each of these compositions were precisely weighed into a DSC dish made of aluminium, and the dish was placed on the right sensor of the measurement cell which was flushed with nitrogen for 5 minutes. A dish containing a polymerized sample of the respective composition was placed on the left sensor to serve as a reference. The recording of the DSC device was started 2.0 minutes after the dish had been placed on the sensor, and after 1.0 minute, radiation was initiated. An waveguide (EXFO Omnicure Series 2000) with an UV filter in the wavelength range λ=320-500 nm was used as the radiation source. The measurement was stopped when the DSC line had become constant. All measurements were carried out under nitrogen.

As results of the DSC measurement, the time of maximum heat flow $t_{max}$ (corresponding to the period of time until the highest polymerization rate in [s] is reached), the area of the peak ΔH (corresponding to the quantity of heat set free in the course of polymerization in [J/g]), and the height of the peak h (in [mW/mg]) were determined. The Double Bound Conversion was calculated from the area of the peak ΔH, the molecular weight MG of the monomers, and the theoretical polymerization heat (ΔH$_o$) of the respective monomers according to the following equation (1):

$$DBC\ [\%] = \frac{\Delta H}{\Delta H_0} \cdot 100 \tag{1}$$

ΔH polymerization heat [J/mol] (area of the peak)
ΔH$_0$ theoretical polymerization heat of the individual component [J/mol]

Moreover, the polymerization rate R$_p$ can be calculated as follows from the height of the peak, the theoretical polymerization heat, and the density ρ of the resin (formula 2):

$$R_P = \frac{h \times \rho}{\Delta H_{0P}} \tag{2}$$

R$_P$ polymerization rate [mol l$^{-1}$ s$^{-1}$]
h height of the peak [mW/mg]
ρ density of the resin [g/dm$^3$]

The results of the measurements are listed in Table 1 below.

TABLE 1

Results for $t_{max}$, R$_p$, and DBC of the individual monomers

| Example - Monomer | Functionalities | $t_{max}$ [s] | R$_p$ × 10$^3$ [mol/l · s] | DBC [%] |
|---|---|---|---|---|
| E1 - DVE | 1 | 35 | 36 | 58 |
| E2 - HVE | 1 | 37 | 35 | 44 |
| E3 - PAVE | 1 | 32 | 48 | 52 |
| E4 - AVE | 2 | 15 | 198 | 79 |

TABLE 1-continued

Results for $t_{max}$, $R_p$, and DBC of the individual monomers

| Example - Monomer | Functionalities | $t_{max}$ [s] | $R_p \times 10^3$ [mol/l·s] | DBC [%] |
|---|---|---|---|---|
| E5 - SEVE | 2 | 22 | 99 | 82 |
| E6 - KVE | 2 | 15 | 173 | 86 |
| E20 - TFVE | 3 | 33 | 23 | 52 |
| E21 - TUVE | 2 | 37 | 105 | 85 |
| E22 - EGDVC | 2 | 12 | 213 | 79 |
| E23 - BDDVC | 2 | 14 | 173 | 80 |
| E24 - HDDVC | 2 | 17 | 150 | 83 |
| E25 - GTVC | 3 | 9 | 75 | 45 |
| E26 - DEGDVC | 2 | 17 | 127 | 68 |
| E27 - PEGDVC | 2 | 28 | 43 | 62 |
| E28 - CEVC | 1 | 21 | 59 | 75 |
| E29 - EVC | 1 | 23 | 47 | 68 |
| E30 - RiTVC | 3 | 16 | 67 | 51 |
| E31 - HRiTVC | 3 | 14 | 82 | 89 |
| E32 - DEG(PLAVC)$_2$ | 2 | 14 | 65 | 52 |
| E33 - DMEDDVCA | 2 | 16 | 117 | 74 |
| E35 - JAVM | 2 | 25 | 186 | 74 |
| E36 - EAVM | 3 | 36 | 23 | 98 |
| E37 - SMEVCA | 1 | 21 | 75 | 76 |
| E38 - MHADVC | 2 | 10 | 91 | 70 |
| E39 - MVCA | 1 | 14 | 73 | 81 |
| E40 - AMVCA | 1(2) | 6 | 165 | 82 |
| E41 - VCPDE | 1 | 11 | 155 | 95 |
| E46 - EPEVC | 1 | 14 | 61 | 90 |
| E47 - EBVCAEP | 2 | 7 | 74 | 78 |
| E48 - DEVP | 1 | 20 | 33 | 90 |
| E49 - DVEP | 2 | 27 | 127 | 89 |
| E50 - TVP | 3 | 23 | 10 | 75 |
| C1 - HDDA | 2 | 7 | 247 | 87 |
| C2 - TTA | 3 | 5 | 98 | 47 |
| C3 - ETA | 3 | 6 | 46 | 78 |
| C4 - PEG - DA | 2 | 5 | 98 | 94 |
| C5 - BDMA | 2 | 22 | 91 | 51 |

It can be seen that the compositions of those examples where difunctional monomers of formula (I) were used cure with generally good to very good polymerization rates $R_p$. As expected, most of the monofunctional monomers cured slower, but still had polymerization rates in the range of the di- and trifunctional comparative examples. Only the monomers of the examples 20, 36, and especially 50, cured significantly slower, which, in the case of the first two monomers, is assumed to be due to the low mobility of the high molecular monomers and the thus great distance between the vinyl ester groups, and, in the case of example 50, is assumed to be due to a stabilizing effect of the triphosphate, even though example 50 is trifunctional. In the light of that, the good performances of the difunctional phosphate ester of example 49, but also of the "monofunctional" monomers of the examples 40 and 41 are somewhat surprising. In the case of the latter two, this is assumed to be due to the presence of an additional acryloyl group in example 40 (which is why the monomer is actually difuntional in this experiment), on the one hand, and to the phosphonic acid group and the low molecular weight in example 41, on the other hand. Comparing monomers of the same size having the same number of functional groups, e.g. E22 and C5 or E23 and C1, it can easily be seen that the reactivity of the new monomers lies between that of highly reactive acrylates and that of those methacrylates which have been used for implants up to now. Almost all compositions of the present invention reach the polymerization rates of the comparative examples or, in many cases, even show higher polymerization rates.

The values for $t_{max}$ of the compositions of the present invention are for the most part higher than those of most comparative examples (except for C5, a methacrylate, methacrylates being preferred to acrylates in most cases in practice), but are in a range which is acceptable for the practical implementation of the invention, especially since, in preferred compositions of the invention, at least 35%, more preferably 50%, of di- or polyfunctional and thus rapidly curing vinyl esters are used as cross-linkers anyway. The examples 40, 47, and 25 show the best performances of all compositions of the invention and are in the range of the most rapidly initiating mixtures of the comparative examples.

The Double Bound Conversions DBC of all the compositions tested were in the range of those of the comparative examples, the phosphonic acid derivative of example 41 yielding the best value. Moreover, it is noticeable that the two difunctional vinyl phosphates of the examples 48 and 49 also yield very high DBC values, the trifunctional phosphate ester of example 50 also yielding an above-average result. The tested compositions of the invention are therefore suitable for the economic preparation of commercial products. Apart from that, it could also be shown that vinyl esters which are known to show relatively low reactivities—also in their carbonate, carbamate and phosphate forms—show surprisingly high reactivities in mass polymerization reactions which are comparable to those of (meth)acrylates, which serve as a yardstick and are commercially widespread.

Toxicity Tests

A) Osteoblast Cells

In order to assess toxicity, osteoblast-like cells MC3T3-E1 (source: ATCC CRL-2596) were used. At first, the adherent cells were separated from each other and from the bottom of the petri dishes using pronase, and were then mixed with freshly prepared medium consisting of commercially available Minimal Essential Medium Eagle's alpha Modification (αMEM), supplemented with additional glucose from originally 1 g/l to a glucose concentration of 4.5 g/l as well as with 10% FCS (fetal calf serum), 30 μg/ml gentamycin (broad-spectrum antibiotic), L-glutamine (400 mg/l), and ascorbic acid (50 mg/l), so as to obtain a cell concentration of 40,000 cells/ml. 1 ml of this cell suspension was precharged into each well (diameter 1.9 cm) of multi-well plates.

The multi-well containing the cells was incubated for 5 days at 37° C. under a humid atmosphere with 5% $CO_2$ together with increasing amounts of the monomers used in the examples and comparative examples. Then the cells were washed with phosphate-buffered physiological saline and frozen before the measurements, in order to break up the cells. After thawing of the cells, the amount of deoxyribonucleic acid, which is proportional to the cell count, was determined by staining with a fluorescent dye, measuring the fluorescence at 460 nm (after excitation at 360 nm) and comparing the value to a calibration curve previously prepared. The interpolated concentration, at which, compared to the control, half of the cells had survived was referred to as "in vitro LC50". The results are listed in Table 2 below.

TABLE 2

Results of the toxicity tests with osteoblasts

| Monomer | In vitro LC50 × $10^4$ [mol/l] |
|---|---|
| DVE | >100 |
| HVE | >100 |
| PAVE | >100 |
| AVE | >100 |
| SEVE | >100 |
| KVE | >100 |
| DVMPL | >100 |
| TFVE | >100 |
| TUVE | >100 |
| EGDVC | >100 |

TABLE 2-continued

Results of the toxicity tests with osteoblasts

| Monomer | In vitro LC50 × $10^4$ [mol/l] |
|---|---|
| BDDVC | >100 |
| HDDVC | >100 |
| GTVC | >100 |
| DEGDVC | >100 |
| PEGDVC | >100 |
| CEVC | >100 |
| EVC | >100 |
| HRiTVC | >100 |
| DEG(PLAVC)$_2$ | >100 |
| DMEDDVCA | >100 |
| JAVM | >100 |
| EAVM | >100 |
| SMEVCA | >100 |
| MHADVC | >100 |
| MVCA | >100 |
| AMVCA | <0.1 |
| VCPDE | >100 |
| EPEVC | >100 |
| EBVCAEP | >100 |
| DEVP | >100 |
| DVEP | >100 |
| TVP | >100 |
| Reference: HDDA | <0.1 |
| Reference: TTA | <0.1 |
| Reference: ETA | 0.7 |
| Reference: PEG-DA | 1.1 |
| Reference: BDMA | <0.1 |

The table shows that the vinyl ester monomers used in the compositions of the present invention are less toxic for osteoblasts than the acrylates of the comparative examples by at least two orders of magnitude. The monomer AMVCA, N-acryloyl-N-methoxy vinyl carbamate, of the present invention is the only exception which, due to the acryloyl group contained therein, is similarly toxic as the majority of the comparative examples. This underlines and confirms the aim of the present invention of avoiding the use of toxic acrylates as monomers for polymers which are to be used in vivo. The novel compound N-acryloyl-N-methoxy vinyl carbamate of the invention, which is a valuable monomer for diverse applications due to its polymerization characteristics, may thus be used only in a limited way in compositions of the present invention according to claim 1, because one has to make sure that no residual monomers are contained in the final polymer product. This may be assured, for example, by means of a post-treatment of the polymer such as by extraction, re-precipitation, or the like.

B) Endothelial Cells

For an additional toxicity test of monomers of formula (I), human umbilical vein endothelial cells (HUVEC) were used. After trypsinating the confluent primary cultures, the cells were suspended in commercial Medium 199 with 20% fetal calf serum, put into 96-well cell culture plates in a concentration of 40,000 cells/cm$^2$, and cultivated until they were confluent again (37° C., 5% $CO_2$). The cell supernatants were then lifted, and the endothelial cells were incubated for 24 hours with increasing monomer concentrations (0.1 nM to 1 mM in Medium 199 with 10% fetal calf serum). The influence on cell proliferation was examined by means of a non-radioactive cell proliferation and cytotoxicity test (EZ4U, Biomedica, Vienna). This test is based on the conversion by living cells of colorless tetrazolium salts into intensively colored formazan derivatives. The photochemically measured staining is proportional to the number of living cells in the sample. Thus, the influence of the test substances on the proliferation of the cells may be photometrically determined. Endothelial cells which had been cultivated without the addition of monomer solutions were used as a growth control. Table 3 below shows those monomer concentrations which yielded a half-maximum proliferation inhibition, $C_{max1/2}$.

TABLE 3

Toxicity tests with endothelial cells

| Monomer | $C_{max1/2}$ [µmol/l] |
|---|---|
| DVE | >1000 |
| HVE | >1000 |
| PAVE | >1000 |
| AVE | >1000 |
| SEVE | >1000 |
| KVE | >1000 |
| DVMPL | >1000 |
| Reference: HDDA | 20 |
| Reference: TTA | 10 |
| Reference: ETA | 100 |
| Reference: PEG-DA | 500 |
| Reference: BDMA | 40 |

This table clearly shows that the toleration of the vinyl ester monomers of formula (I) used in the compositions of the present invention by cells is better than that of acrylates by at least two orders of magnitude.

Biocompatibility Tests

A) Preparation of the Sample Bodies

In order to assess biocompatibility, the compositions of the examples E7 to E19 and of the comparative examples C6 to C8 were used to prepare sample bodies.

The mixtures were cast into a silicone mold in order to prepare small circular plates, and were cured under nitrogen atmosphere on a UV facility (Hg high-pressure lamp, unfiltered, 1000 W). The thus obtained sample bodies were extracted with organic solvents and water in an ultrasonic bath in order to remove residual monomers. The extracted polymer bodies were sterilised by irradiation with UV light.

As a further reference, i.e. as comparative example 9, a polycaprolactone of MW 1400, available from Sigma Aldrich, was melted and also cast into the silicone mold to obtain a plate.

B) Tests with Osteoblast Cells

For examining biocompatibility, osteoblast-like cells MG-63 (ATCC CRL-1427), which were prepared in the same way as described for the toxicity test, suspended in the same medium, and distributed to the wells of multi-well plates, in which the sample bodies had been placed, in the same way as described above, were used.

The multi-well was incubated in the presence of the sample bodies for 3 days at 37° C. in a humid atmosphere with 5% $CO_2$. Then, the metabolic activity of the living cells (cell vitality) was photometrically determined by means of the EZ4U test (Biomedica, Vienna) in the same way as described before for the toxicity tests and related to the cell activity on cell culture dishes, cells cultivated on commercially available culture dishes being used as growth controls. In Table 4 below, the number of cells contained in the sample is listed for each sample body example as a percentage of the control (control=100% cells).

TABLE 4

Biocompatibility with osteoblasts

| Example - Monomers of the sample bodies | Number of cells (% of the control) |
|---|---|
| E7 - AVE | 109 |
| E8 - SEVE | 192 |
| E9 - KVE | 130 |
| E10 - AVE:HVE (1:1) | 92 |
| E11 - AVE:HVE (3:1) | 102 |
| E12 - AVE:DVE (1:1) | 125 |
| E13 - AVE:DVE (3:1) | 130 |
| E14 - AVE:PAVE (1:1) | 128 |
| E15 - AVE:PAVE (3:1) | 112 |
| E16 - AVE:VMDPL (1:1) | 144 |
| E17 - AVE:VMDPL (3:1) | 102 |
| E18 - AVE:MC (20:1) | 124 |
| E19 - AVE:MC (20:1) mod. | 246 |
| C6 - HDDA | 48 |
| C7 - PEG-DA | 24 |
| C8 - TTA:ETA (1:1) | ~1 |
| C9 - PCL | ~1 |

The table clearly shows that the sample bodies of the comparative examples resulted in a significant reduction of the cell count, while the sample bodies prepared from the compositions of the present invention even resulted in cell proliferation.

C) Tests with Endothelial Cells

For the biocompatibility tests, human umbilical vein endothelial cells (HUVEC) were again used. After trypsinating the confluent primary cultures, the cells were suspended in Medium 199 with 20% fetal calf serum (FCS) and put onto the sample body to be tested (40,000 cells/cm$^2$). After 24 hours of cultivation (37° C., 5% CO$_2$), the cell supernatants were lifted, and the endothelial cells were washed with phosphate-buffered saline (PBS) and equilibrated with Medium 199 with 10% FCS for 1 hour. Cell proliferation was then determined by means of an EZ4U test. The proliferation of the endothelial cells on plastic cover-slips which were specifically pretreated in order to improve cell adherence ("Cell culture-treated plastic coverslips", Thermanox®, Fa. Nunc) was measured for comparative purposes and taken as 100%. In Table 5, the data are listed as mean values of multiple determinations.

TABLE 5

Biocompatibility with endothelial cells

| Example - Monomers of the sample bodies | Cell count (% of the control) |
|---|---|
| E7 - AVE | 73 |
| E8 - SEVE | 70 |
| E9 - KVE | 69 |
| E10 - AVE:HVE (1:1) | 75 |
| E11 - AVE:HVE (3:1) | 68 |
| E12 - AVE:DVE (1:1) | 63 |
| E13 - AVE:DVE (3:1) | 62 |
| E14 - AVE:PAVE (1:1) | 90 |
| E15 - AVE:PAVE (3:1) | 68 |
| E16 - AVE:VMDPL (1:1) | 110 |
| E17 - AVE:VMDPL (3:1) | 82 |
| E18 - AVE:MC (20:1) | 68 |
| E19 - AVE:MC (20:1) mod. | 194 |
| C6 - HDDA | 59 |
| C7 - PEG-DA | 14 |
| C8 - TTA:ETA (1:1) | 24 |
| C9 - PCL | 1 |

It can be seen that up to double the number of cells found on a plastic having a pre-treated surface for specifically enhancing cell adherence had accumulated on the polymer sample bodies prepared from the compositions of the present invention. After appropriate surface treatment, the polymers of the present invention could easily yield better values than the comparison, which becomes evident from example 19. Contrary to that, the polymers prepared from the comparative examples all yield (significantly) poorer results. Only HDDA yields a value coming close to the lowest values of the examples.

The morphology of adherent endothelial cells on sample bodies made of the compositions of example 7 and comparative example 2 was examined by means of scanning electron microscopy. The photos with 350× (FIGS. 1a, 1b) or 150× (FIG. 1c) magnification are shown in FIG. 1. In the acrylate comparison in FIG. 1a (polymer of comparative example 2), only individual cells, hardly bound to the sample body (which becomes clear from their round form), can be seen. Contrary to that, the cells adhere well to the plastic produced from composition E7 of the present invention (which becomes clear from to their regular form in FIG. 1b), and numerous cells had bound to the sample body, which can clearly be seen in FIG. 1c.

Mechanical Properties

Circular sample bodies having a diameter of 5 mm and a height of 1 mm, whose mechanical properties were measured by means of nanoindentation in the following way, were formed using the compositions of the examples 7 to 17, 20 to 27, 30 to 32, 33, 35, 36, and 38 to 45 according to the present invention as well as those of the comparative examples C1 to C4, C8, and C9.

The indentation hardness $H_{IT}$ and the indentation modulus $E_{IT}$ were determined using the Nanoindenter XP, MTS Systems Inc. To this end, the sample bodies were stuck to an aluminium block by means of a two-component adhesive and grinded and polished by means of abrasive papers having different degrees of coarseness. With a diamond pyramid according to Berkovich, the indentation was carried out using an indentation depth of 2 μm and an indentation rate of 0.1 μm/s. After a holding time of 30 seconds at maximum load, the sample bodies were relieved again. The indentation modulus $E_{IT}$ can now be calculated from the slope of the relief curve at maximum load:

$$E_{IT} = \frac{1 - (v_s)^2}{\frac{1}{E_r} - \frac{1 - (v_i)^2}{E_i}} \quad (3)$$

$v_{s,i}$ Poisson ratio of the sample and the indenter (for all samples $v_s=0.35$)
$E_i$ modulus of the indenters [MPa]
$E_r$ reduced modulus of the indentation contact [MPa]
wherein:

$$E_r = \frac{\sqrt{\pi} \cdot S}{2\sqrt{A_p}} \quad (4)$$

S contact strength [N/m]
$A_p$ projected contact area [m$^2$]

The indentation hardness $H_{IT}$ was calculated from the maximum force $F_{max}$ (W. C. Oliver, G. M. Pharr, J. Mater. Res. 7, 1564 (1992), and ISO 14577):

$$H_{IT} = \frac{F_{max}}{24.5 \cdot h_c^2} \quad (5)$$

$F_{max}$ maximum strength [N]
wherein:

$$h_c = h_{max} - \epsilon(h_{max} - h_r) \quad (6)$$

$h_{max}$ indentation depth at $F_{max}$ [m]
$h_r$ intersection of the tangent of the relief curve at maximum load with the x-axis x-Achse [m]
$\epsilon$ indenter constant In Table 3, the results are listed as mean values of multiple determinations.

TABLE 3

Mechanical properties

| Example - Monomers of the sample body | Hardness [MPa] | E-modulus [MPa] |
|---|---|---|
| E7 - AVE | 188 | 1937 |
| E8 - SEVE | 113 | 1304 |
| E9 - KVE | 139 | 1496 |
| E10 - AVE:HVE (1:1) | 90 | 1456 |
| E11 - AVE:HVE (3:1) | 126 | 1705 |
| E12 - AVE:DVE (1:1) | 44 | 587 |
| E13 - AVE:DVE (3:1) | 107 | 1287 |
| E14 - AVE:PAVE (1:1) | 128 | 1558 |
| E15 - AVE:PAVE (3:1) | 156 | 1628 |
| E16 - AVE:DVMPL (1:1) | 147 | 1412 |
| E17 - AVE:DVMPL (3:1) | 158 | 1592 |
| E20 - TFVE | 2.5 | 18 |
| E21- TUVE | 109 | 2335 |
| E22 - EGDVC | 298 | 3910 |
| E23 - BDDVC | 214 | 2553 |
| E24 - HDDVC | 175 | 2017 |
| E25 - GTVC | 396 | 4688 |
| E26 - DEGDVC | 107 | 1605 |
| E27 - PEGDVC | 9 | 187 |
| E30 - RiTVC | 98 | 512 |
| E31- HRiTVC | 5 | 31 |
| E32 - DEG(PLAVC)$_2$ | 270 | 2992 |
| E33 - DMEDDVCA | 297 | 4344 |
| E35 - JAVM | 142 | 2922 |
| E36- EAVM | 3.2 | 20 |
| E38 - MHADVC | 319 | 4115 |
| E39 - MVCA | 108 | 1315 |
| E40 - AMVCA | 301 | 3875 |
| E41 - VCPDE | 125 | 1424 |
| E42 - EGDVC:CEVC (5:1) | 152 | 2310 |
| E43 - EGDVC:EVC (5:1) | 142 | 2108 |
| E44 - DMEDDVCA:PDVCA (5:1) | 161 | 2468 |
| E45 - DMEDDVCA:SMEVCA (5:1) | 189 | 2576 |
| E46 - EPEVC | 47 | 446 |
| E47- EBVCAEP | 167 | 1832 |
| E48 - DEVP | 76 | 669 |
| E49 - DVEP | 189 | 2532 |
| E50 - TVP | 267 | 2856 |
| C1 - HDDA | 131 | 1791 |
| C2 - TTA | 296 | 3386 |
| C3 - ETA | 17 | 349 |
| C4 - PEG-DA | 11 | 212 |
| C8 - TTA:ETA (1:1) | 78 | 691 |
| C9 - PCL | 49 | 722 |

It becomes clear from the table that polymer bodies showing a wide range of different hardness and elasticity values can be produced from the compositions of the present invention. By the addition of co-monomers or optional additives such as softeners, fillers, etc., and/or by appropriate post-treatments such as heat treatment and/or extraction steps after the polymerization of the compositions, this variety may still be significantly increased. Thus, it is easily possible to achieve better results than those of the comparative examples in all respects, which means that the compositions of the present invention may be used for different applications in or on the human or animal body or as coating materials, for example for medical products, or for materials to be used in contact with food or drugs. The industrial applicability of the monomers and compositions of the present invention, e.g. for the preparation of tissue supportive materials or tissue substitute materials, is therefore beyond any doubt.

The invention claimed is:

1. A method for preparing a body implant comprising a biodegradable, biocompatible, cross-linked polymer, which method comprises the following steps:
   providing a polymerization-curable composition comprising:
   (a) 5 to 100% by weight of one or more vinyl ester monomers of the general formula (II):

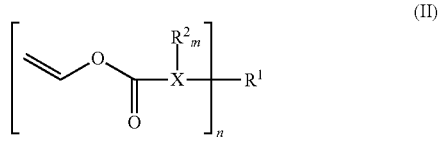

(II)

wherein:
   X is a heteroatom selected from the group consisting of oxygen, sulfur, nitrogen, and phosphorus;
   n is 1 to 1000, at least 20% of the n being ≥2;
   the groups $R^1$ are independently selected from:
   (i) hydrogen; straight, branched or cyclic, saturated or unsaturated, n-valent hydrocarbon groups which have 1 to 30 carbon atoms, which optionally comprise one or more heteroatoms selected from oxygen, sulfur, nitrogen, and phosphorus within the carbon chains and/or at the end of the carbon chains thereof, and which are optionally substituted with one or more substituents selected from the group consisting of —OH, —COOH, —CN, —CHO), and =O, and
   (ii) n-valent radicals of biodegradable, biocompatible oligomers and polymers selected from the group consisting of polysaccharides, polypeptides, polyamides, polyesters, polycarbonates, polyethers, and fatty acid derivatives;
   m is an integer from 0 to 4; and
   the groups $R^2$ are selected from the group consisting of —OH, =O, and
   the options listed for $R^1$;
   (b) 0 to 50% by weight of one or more a-olefin co-monomers;
   (c) 0 to 10% by weight of one or more polymerization initiators selected from the group consisting of thermal initiators and photoinitiators; and
   (d) 0 to 95% by weight of one or more solvents selected from the group consisting of water, lower alcohols, ether, ketone, ester, amide and hydrocarbon solvents;
   shaping the composition; and
   thermally or photochemically polymerizing and thus curing the shaped composition to provide the body implant.

2. The method according to claim 1, wherein the vinyl ester monomer of the general formula (II) accounts for 50 mole percent of all monomers contained in the polymerization-curable composition.

3. The method according to claim 1, wherein at least 35 mole percent of all vinyl ester monomers are difunctional or higher functional, cross-linking monomers in which n is ≥2.

4. The method according to claim 1, wherein the a-olefin co-monomers used as the component (b) are selected from: (meth)acrylic acid, (meth)acrylic anhydride, (meth)acrylic acid glycidyl ester, (meth)acryloyloxy succinic acid anhydride, (meth)acryloyloxymethyl succinic anhydride, (meth)acrylic acid 2-oxo -1 ,3-dioxo lanylmethyl ester, vinyl succinic anhydride, vinylene carbonate, maleic acid, maleic anhydride, fumaric acid and vinylpyrrolidone.

5. The method according to claim 1, wherein the polymerization-curable composition comprises, as a further component (e), one or more additives selected from the group consisting of polymerization sensitizers, polymerization inhibitors, stabilizers, modifying agents, softeners, dyeing agents, bioactive agents, cells, thickening agents, and fillers.

6. The method according to claim 5, wherein the bioactive agents are selected from the group consisting of drugs, proteins, antibodies, and ligands.

7. The method according to claim 1, wherein one or more additives are covalently bound to monomers or co-monomers.

8. The method according to claim 7, wherein at least one additive covalently bound to monomers or co-monomers is a bioactive agent.

9. The method according to claim 1, wherein part of the polymerization-curable composition is pre-cured, with which the remaining uncured composition is mixed, and the mixture is cured.

10. The method according to claim 1, wherein the polymerization is carried out in the course of a generative manufacturing process.

11. The method according to claim 1, wherein the shaped composition is subjected to one or more post-treatment step(s) after curing.

12. The method according to claim 11, wherein the post-treatment steps are selected from the group consisting of post-curing, heat treatment, extraction, re-precipitation, and surface treatment steps.

13. The method according to claim 1, wherein at least one vinyl ester monomer is selected from the group consisting of 1,4-butanediol bis(vinyl carbonate), 2-cyanoethyl vinyl carbonate, N,N'-dimethyl-1,2-ethylenediamine bis(vinyl carbamate), sarcosine methyl ester vinyl carbamate, N,O-bis(vinyloxycarbonyl)-N- methylhydroxylamine, N-methoxy vinyl carbamate, N-acryloyl-N-methoxy vinyl carbamate, vinyloxycarbonylphosphonic acid diethyl ester, 2-(diethoxyphosphoryloxy)ethylamine vinyl carbamate, ethyl bis[2-(vinyloxycarbonylamino)ethyl] phosphate, and divinyl ethyl phosphate.

14. The method according to claim 1, wherein the shaping step is conducted in vivo.

15. The method according to claim 1, wherein the shaping step is conducted in vivo while the composition is contained in a degradable container.

16. The method according to claim 1, wherein the vinyl ester monomer of the general formula (II) accounts for 50 mole percent of all monomers contained in the polymerization-curable composition, and at least 35 mole percent of all vinyl ester monomers are difunctional or higher functional, cross-linking monomers in which n is ≥2.

* * * * *